United States Patent
Shouhi et al.

(10) Patent No.: US 11,048,112 B2
(45) Date of Patent: Jun. 29, 2021

(54) GLASS STRUCTURE

(71) Applicant: SEKISUI CHEMICAL CO., LTD., Osaka (JP)

(72) Inventors: Hajime Shouhi, Otsu (JP); Shougo Yoshida, Konan (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 16/650,061

(22) PCT Filed: Sep. 28, 2018

(86) PCT No.: PCT/JP2018/036489
§ 371 (c)(1),
(2) Date: Mar. 24, 2020

(87) PCT Pub. No.: WO2019/066042
PCT Pub. Date: Apr. 4, 2019

(65) Prior Publication Data
US 2020/0292858 A1    Sep. 17, 2020

(30) Foreign Application Priority Data

Sep. 29, 2017 (JP) .............................. JP2017-192251
Nov. 20, 2017 (JP) .............................. JP2017-222819

(51) Int. Cl.
*G02B 5/22*    (2006.01)
*G02F 1/1335*    (2006.01)
(Continued)

(52) U.S. Cl.
CPC ......... *G02F 1/1335* (2013.01); *C07D 209/08* (2013.01); *C07D 251/72* (2013.01);
(Continued)

(58) Field of Classification Search
CPC ........ G02F 1/1335; G02F 1/1334; G02F 1/15; G02F 1/13; G02B 5/22
See application file for complete search history.

(56) References Cited

U.S. PATENT DOCUMENTS 5,296,519 A    3/1994  Otsuka
6,259,559 B1 *  7/2001  Kobayashi ........ B32B 17/10036
                                              359/485.02
(Continued)

FOREIGN PATENT DOCUMENTS

EP    0 913 446    5/1999
JP    4-134065    5/1992
(Continued)

OTHER PUBLICATIONS

International Search Report (ISR) dated Jan. 8, 2019 in International (PCT) Application No. PCT/JP2018/036489.
(Continued)

*Primary Examiner* — Donald L Raleigh
(74) *Attorney, Agent, or Firm* — Wenderoth, Lind & Ponack, L.L.P.

(57) ABSTRACT

A glass structure 10 includes a pair of glass plates 11 and 12, a light control body 13 disposed between the pair of glass plates 11 and 12, and an ultraviolet absorbing layer 14 disposed between the light control body 13 and one of the glass plates 11. The ultraviolet absorbing layer 14 has a maximum transmittance of 10% or less in a wavelength region of 370 nm or more and 400 nm or less and a maximum transmittance of 50% or more in a wavelength region of more than 400 nm and 420 nm or less, and a ratio of a transmittance at 405 nm to a transmittance at 395 nm is 12 or more.

16 Claims, 1 Drawing Sheet

(51) Int. Cl.
 *C07D 209/08* (2006.01)
 *C07D 251/72* (2006.01)
 *G02F 1/1334* (2006.01)
 *G02F 1/15* (2019.01)

(52) U.S. Cl.
 CPC ............ *G02B 5/22* (2013.01); *G02F 1/1334* (2013.01); *G02F 1/15* (2013.01)

(56) References Cited

U.S. PATENT DOCUMENTS

2008/0157025 A1 7/2008 Fritzsche et al.
2013/0194658 A1* 8/2013 Tamura ................ G02B 5/003
 359/352
2015/0301367 A1 10/2015 Mennig

FOREIGN PATENT DOCUMENTS

| | | |
|---|---|---|
| JP | 10-17337 | 1/1998 |
| JP | 2001-83554 | 3/2001 |
| JP | 2008-528657 | 7/2008 |
| JP | 2010-145856 | 7/2010 |
| JP | 2012-58643 | 3/2012 |
| WO | 2009/065490 | 5/2009 |
| WO | 2012/023616 | 2/2012 |
| WO | 2017/033872 | 3/2017 |
| WO | 2018/098074 | 5/2018 |

OTHER PUBLICATIONS

Extended European Search Report dated Apr. 23, 2021, in corresponding European Patent Application No. 18861308.7.

\* cited by examiner

GLASS STRUCTURE

TECHNICAL FIELD

The present invention relates to a glass structure including a light control body.

BACKGROUND ART

Conventionally, light control bodies to which a voltage is applied to provide a changed light transmittance have been widely known. Examples of the light control bodies include a light control body including electrodes and a liquid crystal material or an electrochromic material and the like interposed between the electrodes. When the light control bodies are used, the application of a voltage switches between transparence and opacity, whereby the light control bodies have been considered to be applied to glass for automobiles and glass for outer windows of buildings, and the like in recent years from the viewpoints of control of an internal temperature and privacy protecting and the like.

When the light control body is applied to these glasses, a glass structure including two glass plates and a light control body interposed between the glass plates has been known, as disclosed in PTL 1, for example. From the viewpoint of securing adhesiveness, and the like, an adhesion layer has also been considered to be disposed between a glass plate and a light control body.

As the glass for automobiles, laminated glass obtained by interposing an intermediate film between two glass plates for integrating has also been widely known. In the laminated glass, the intermediate film is formed of a thermoplastic resin such as a polyvinyl acetal. An ultraviolet absorber may be blended in an intermediate film in order to reduce the burden on the eyes or skins of crews (see, for example, PTL 2 and 3).

CITATION LIST

Patent Literatures

PTL 1: JP 2010-145856 A
PTL 2: JP 1110-17337 A
PTL 3: WO 2012/023616 A1

SUMMARY OF INVENTION

Technical Problem

In the meantime, when the light control body including the liquid crystal material or the electrochromic material and the like is exposed to sunlight, the light control body may be rapidly deteriorated. Meanwhile, in order to secure high visibility, high light permeability in a visible light range when the light control body is switched to transparence is required for the glass structure to which the light control body is applied. Therefore, high transparency is required also for the glass plate and the adhesion layer for bonding the glass plate and the light control body to each other, and thus, it is difficult to shield the sunlight by using the glass plate and the adhesion layer and the like.

The present invention has been made in view of the above situation, and it is an object of the present invention to provide a glass structure which prevents the deterioration of a light control body caused by sunlight while securing the transparency of the glass structure.

Solution to Problem

As a result of intensive studies, the present inventors found that a light control body including a liquid crystal material or an electrochromic material and the like is markedly deteriorated by long-wavelength ultraviolet rays among sunlight. The present inventors found that the problems can be solved by providing an ultraviolet absorbing layer in which a transmittance in a specific wavelength region is designed in a predetermined range between a glass plate and a light control body, and completed the following present invention.

That is, the present invention provides the following [1] to [16].

[1] A glass structure comprising: a pair of glass plates; a light control body disposed between the pair of glass plates; and an ultraviolet absorbing layer disposed between the light control body and one of the glass plates, wherein: the ultraviolet absorbing layer has a maximum transmittance of 10% or less in a wavelength region of 370 nm or more and 400 nm or less and a maximum transmittance of 50% or more in a wavelength region of more than 400 nm and 420 nm or less; and a ratio of a transmittance at 405 nm to a transmittance at 395 nm is 12 or more.

[2] The glass structure according to the above [1], wherein a ratio of a thickness of the light control body to that of the ultraviolet absorbing layer is 0.5 to 10.5.

[3] The glass structure according to the above [1] or [2], wherein the ultraviolet absorbing layer comprises at least one thermoplastic resin selected from the group consisting of a polyvinyl acetal resin, an ethylene-vinyl acetate copolymer resin, and an ionomer resin.

[4] The glass structure according to any one of the above [1] to [3], wherein the ultraviolet absorbing layer comprises a polyvinyl acetal resin and a plasticizer.

[5] The glass structure according to any one of the above [1] to [4], wherein the light control body comprises any one of a liquid crystal layer and an electrochromic layer.

[6] The glass structure according to any one of the above [1] to [5], wherein the ultraviolet absorbing layer comprises an ultraviolet absorber.

[7] The glass structure according to the above [6], wherein the ultraviolet absorber comprises at least one selected from the group consisting of an indole-based compound, a benzotriazole-based compound, and a coumarin-based compound.

[8] The glass structure according to the above [7], wherein the indole-based compound is a compound represented by the following formula (1),

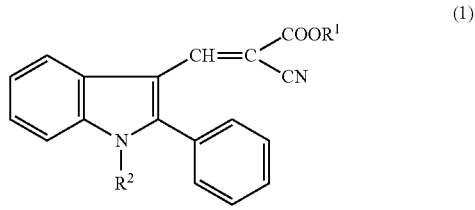

wherein:
R$^1$ represents an alkyl group having 1 to 3 carbon atoms; and
R$^2$ represents a hydrogen atom, an alkyl group having 1 to 10 carbon atoms, or an aralkyl group having 7 to 10 carbon atoms.

[9] The glass structure according to the above [7] or [8], wherein the benzotriazole-based compound is a compound represented by the following formula (2),

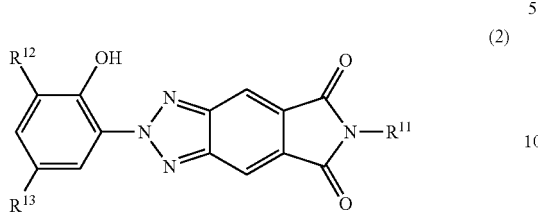

wherein:
$R^{11}$ represents an alkyl group having 1 to 10 carbon atoms; and
$R^{12}$ and $R^{13}$ each independently represent a hydrogen atom, an alkyl group having 1 to 10 carbon atoms, or an aralkyl group having 7 to 12 carbon atoms.

[10] The glass structure according to any one of the above [7] to [9], further comprising a compound having a highest absorption maximum in a wavelength region of 330 to 380 nm.

[11] The glass structure according to the above [10], wherein the compound having a highest absorption maximum in a wavelength region of 330 to 380 nm is a compound represented by the following formula (3),

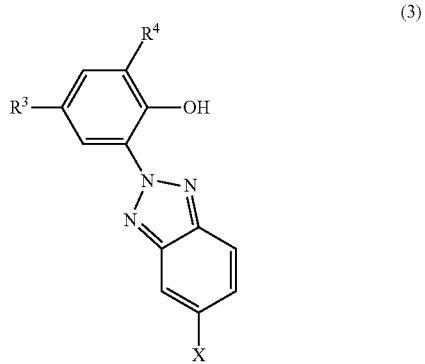

wherein:
$R^3$ represents a hydrogen atom, an alkyl group having 1 to 8 carbon atoms, or an alkoxycarbonylalkyl group having 4 to 20 carbon atoms;
$R^4$ represents a hydrogen atom or an alkyl group having 1 to 8 carbon atoms; and
X is a chlorine atom or a hydrogen atom.

[12] The glass structure according to any one of the above [1] to [11], further comprising an adhesion layer disposed between the light control body and the other glass.

[13] The glass structure according to the above [12], wherein the adhesion layer comprises at least one thermoplastic resin selected from the group consisting of a polyvinyl acetal resin, an ethylene-vinyl acetate copolymer resin, and an ionomer resin.

[14] The glass structure according to the above [12] or [13], wherein the adhesion layer comprises a polyvinyl acetal and a plasticizer.

[15] The glass structure according to any one of the above [12] to [14], wherein a ratio of a thickness of the light control body to that of the adhesion layer is 0.5 to 10.5.

[16] The glass structure according to any one of the above [1] to [15] used for an outdoor window.

Advantageous Effects of Invention

The present invention provides a glass structure which prevents the deterioration of a light control body caused by sunlight while securing the transparency of the glass structure.

DESCRIPTION OF EMBODIMENTS

Hereinafter, a glass structure of the present invention will be described in detail by referring to an embodiment.

Figure 1:
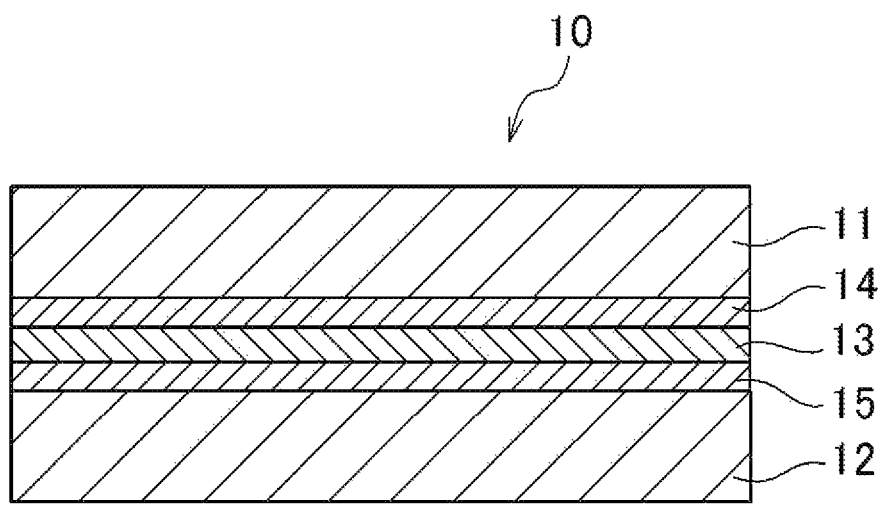
FIG. 1 is a schematic sectional view showing a glass structure according to one embodiment of the present invention.
Figure 2:
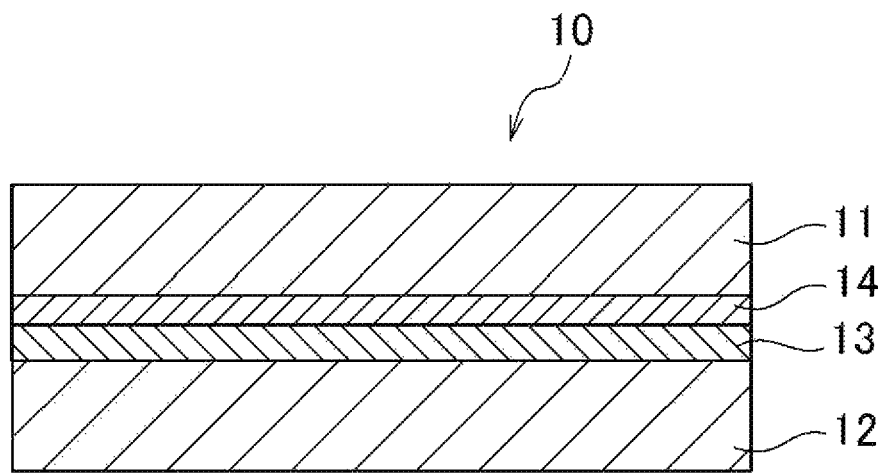
FIG. 2 is a schematic sectional view showing a glass structure according to another embodiment of the present invention.

As shown in FIGS. 1 and 2, a glass structure 10 of the present invention includes a pair of glass plates (may be referred to as "first and second glass plates" respectively) 11 and 12, a light control body 13 disposed between the glass plates 11 and 12, and an ultraviolet absorbing layer 14 disposed between the light control body 13 and the first glass plate 11.

Preferably, the ultraviolet absorbing layer 14 comprises a thermoplastic resin so as to have a function as an adhesion layer (also referred to as a "first adhesion layer") as described later, and bonds the first glass plate 11 and the light control body 13 to each other. As shown in FIG. 2, in the glass structure 10, the light control body 13 may be directly bonded to the second glass plate 12. As shown in FIG. 1, preferably, an adhesion layer (also referred to as a "second adhesion layer") 15 is provided between the light control body 13 and the second glass plate 12, and the light control body 13 is bonded to the second glass plate 12 by the second adhesion layer 15.

The glass structure 10 of the present invention may include the glass plates 11 and 12, the light control body 13, and the ultraviolet absorbing layer 14, or the glass plates 11 and 12, the light control body 13, the ultraviolet absorbing layer 14, and the second adhesion layer 15. The glass structure 10 may include any layers other than these layers. For example, an infrared absorbing layer and the like may be provided between the glass plate 11 and the ultraviolet absorbing layer 14, or between the light control body 13 (or the second adhesion layer 15) and the glass plate 12.

Hereinafter, members of the glass structure will be described in detail.

[Ultraviolet Absorbing Layer and Second Adhesion Layer]

The ultraviolet absorbing layer of the present invention has a maximum transmittance of 10% or less in a wavelength region of 370 nm or more and 400 nm or less and a maximum transmittance of 50% or more in a wavelength region of more than 400 nm and 420 nm or less. In the ultraviolet absorbing layer, a ratio of a transmittance at 405 nm to a transmittance at 395 nm is 12 or more.

For example, the glass structure of the present invention is used such that the first glass plate is disposed on an outdoor side, and sunlight is made incident from the side of the first glass plate. If the maximum transmittance in a wavelength region of 370 nm or more and 400 nm or less exceeds 10%, long-wavelength ultraviolet rays of large amounts transmit the ultraviolet absorbing layer, whereby the light control body is irradiated with the long-wavelength ultraviolet rays. This makes it impossible to sufficiently prevent the deterioration of the light control body. If the maximum transmittance in a wavelength region of more than 400 nm and 420 nm or less is less than 50%, or the ratio of a transmittance at 405 nm to a transmittance at 395 nm is less than 12, visible light near an ultraviolet region is absorbed by the ultraviolet absorbing layer more than necessary, which causes low transparency. When the glass structure is irradiated with sunlight, the glass structure may seem to be colored.

In order to more effectively prevent the deterioration of the light control body caused by the sunlight, the ultraviolet absorbing layer preferably has a maximum transmittance of 7% or less in a wavelength region of 370 nm or more and 400 nm or less, and more preferably 5% or less. The maximum transmittance in a wavelength region of 370 nm or more and 400 nm or less in the ultraviolet absorbing layer is preferably lower from the viewpoint of preventing the deterioration of the light control body, but it is preferably 0.1% or more, and more preferably 0.5% or more in order to suppress yellow.

The ultraviolet absorbing layer preferably has a maximum transmittance of 60% or more in a wavelength region of more than 400 nm and 420 nm or less, more preferably 65% or more, and still more preferably 70% or more. Thus, the maximum transmittance in a wavelength region of more than 400 nm and 420 nm or less is increased to such a high level, which prevents deteriorated transparency of the glass structure caused by the ultraviolet absorbing layer, and also appropriately prevents the glass structure from seeming to be colored. The maximum transmittance in a wavelength region of more than 400 nm and 420 nm or less is preferably higher, and the upper limit thereof is 100%.

In the ultraviolet absorbing layer, the ratio of a transmittance at 405 nm to a transmittance at 395 nm is preferably 15 or more, and more preferably 17 or more. Thus, the ratio of the transmittance is increased to such a high level, which is likely to secure the high transparency of the light control body and to suppress the yellow while more effectively preventing the deterioration of the light control body caused by the sunlight. The ratio of the transmittance is preferably higher. From the viewpoint of suppressing the deterioration of the light control film, the ratio of the transmittance is preferably 400 or less, more preferably 200 or less, and still more preferably 50 or less.

Further, the visible light transmittance of the ultraviolet absorbing layer is preferably higher. Specifically, the visible light transmittance is preferably 70% or more, more preferably 80% or more, and still more preferably 85% or more. The visible light transmittance of the ultraviolet absorbing layer is increased to such a higher level, which is likely to sufficiently secure the transparency of the glass structure. The visible light transmittance means the transmittance of the whole visible light range, and is measured based on JIS R 3106 (1998).

(Ultraviolet Absorber)

The ultraviolet absorbing layer preferably comprises an ultraviolet absorber. More preferably, the ultraviolet absorbing layer comprises a thermoplastic resin, and the ultraviolet absorber is blended in the thermoplastic resin.

In the present invention, the ultraviolet absorber preferably comprises an indole-based compound. In the present invention, the ultraviolet absorber also preferably comprises either a benzotriazole-based compound or a coumarin-based compound. At least one of these compounds is used, whereby the ultraviolet absorbing layer can have a low transmittance in a long-wavelength ultraviolet region without decreasing the transmittance of the visible light range. Therefore, the maximum transmittance and the ratio of the transmittance are likely to be adjusted to a desired range.

The indole-based compound has an indole skeleton, and preferable examples thereof include a compound represented by the following formula (1),

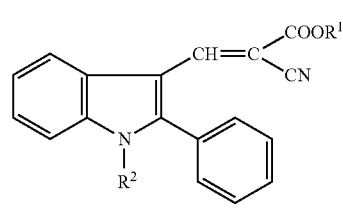

(1)

wherein $R^1$ represents an alkyl group having 1 to 3 carbon atoms; and $R^2$ represents a hydrogen atom, an alkyl group having 1 to 10 carbon atoms, or an aralkyl group having 7 to 10 carbon atoms.

The alkyl groups of $R^1$ and $R^2$ may have a straight chain structure or a branched structure. Examples of $R^1$ in the formula (1) include methyl, ethyl, isopropyl, and n-propyl groups. Among these, $R^1$ is preferably methyl, ethyl, and isopropyl groups. From the viewpoint of light resistance, $R^1$ is more preferably a methyl or ethyl group.

$R^2$ in the formula (1) is preferably an alkyl group having 1 to 10 carbon atoms, and more preferably an alkyl group having 1 to 8 carbon atoms. Examples of the alkyl group having 1 to 10 carbon atoms include methyl, ethyl, isopropyl, n-propyl, isobutyl, n-butyl, pentyl, hexyl, 2-ethyl hexyl, and n-octyl groups. Examples of the aralkyl group having 7 to 10 carbon atoms include benzyl, phenyl ethyl, phenyl propyl, and phenyl butyl groups.

Preferable examples of the benzotriazole compound include a compound represented by the following formula (2):

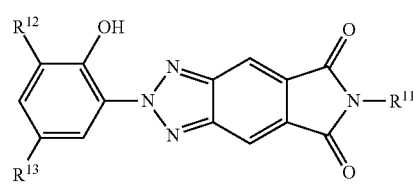

(2)

wherein $R^{11}$ represents an alkyl group having 1 to 10 carbon atoms, and $R^{12}$ and $R^{13}$ each independently represent a hydrogen atom, an alkyl group having 1 to 10 carbon atoms, or an aralkyl group having 7 to 12 carbon atoms.

In the formula (2), the alkyl groups for $R^{11}$, $R^{12}$, and $R^{13}$ may have a straight chain structure or a branched structure. Examples of the alkyl group having 1 to 10 carbon atoms include methyl, ethyl, isopropyl, n-propyl, isobutyl, n-butyl, pentyl, hexyl, 2-ethylhexyl, n-octyl, and 1,1,3,3-tetramethylbutyl groups. Examples of the aralkyl group having 7 to 12 carbon atoms include benzyl, phenylethyl, phenylpropyl, and phenylbutyl groups. The alkyl groups for $R^{11}$, $R^{12}$, and $R^{13}$ preferably have 4 to 10 carbon atoms. In the formula (2), preferably, $R^{12}$ is an aralkyl group and RN is an alkyl group.

Specific examples of the benzotriazole compound include 6-butyl-2-[2-hydroxy-3-(1-methyl-1-phenylethyl)-5-(1,1,3,3-tetramethylbutyl)-phenyl]-pyrrolo[3,4-f][benzotriazole-5,7(2H,6H)-dione. Examples of the commercially available product include TINUVIN CarboProtect (trade name, manufactured by BASF A.G.).

Examples of the coumarin-based compound include known compounds that have been used as the ultraviolet absorber. Examples thereof include Eusorb UV-1990 (trade name, manufactured by Eutec Chemical Co., Ltd.).

The ultraviolet absorbing layer preferably contains at least one ultraviolet absorber selected from the group consisting of the indole-based compound, the benzotriazole-based compound, and the coumarin-based compound, and the content of the ultraviolet absorber is 0.001 to 0.4% by mass based on the total amount of the ultraviolet absorbing layer, for example. The suitable values of the contents of the various ultraviolet absorbers vary depending on the kinds of compounds.

For example, the content of the indole-based compound is preferably 0.001 to 0.1% by mass, based on the total amount of the ultraviolet absorbing layer. In the present invention, the content of the indole-based compound is set to 0.001% by mass or more, whereby the maximum transmittance in a wavelength region of 370 nm or more and 400 nm or less is likely to be adjusted to 10% or less. From such a viewpoint, the content of the indole-based compound is more preferably 0.002% by mass or more, and still more preferably 0.005% by mass.

Further, the content thereof is set to 0.1% by mass or less, whereby such a decrease in the transmittance in a visible light range that is due to coloring provided by the ultraviolet absorber can be prevented. From such a viewpoint, the content of the indole-based compound is more preferably 0.05% by mass or less, and still more preferably 0.03% by mass or less. The suitable value of the content of the coumarin-based compound is selected in the same manner as the suitable value of the content of the indole-based compound.

From the same viewpoint described above, the content of the benzotriazole-based compound is preferably 0.005 to 0.4% by mass based on the total amount of the ultraviolet absorbing layer. The content thereof is more preferably 0.01% by mass or more, and still more preferably 0.02% by mass or more. The content is more preferably 0.3% by mass or less, still more preferably 0.15% or less, and particularly preferably 0.06% by mass or less.

At least two ultraviolet absorbers (first and second ultraviolet absorbers) which are compounds different from each other are preferably used in combination as the ultraviolet absorber.

Specifically, at least compound (hereinafter, also referred to as a "first ultraviolet absorber") selected from the group consisting of the indole-based compound, the benzotriazole-based compound, and the coumarin-based compound, and a compound different from the compound (hereinafter, also referred to as a "second ultraviolet absorber") are preferably used.

For example, the indole-based compound and an ultraviolet absorber other than the indole-based compound (second ultraviolet absorber) are preferably used in combination as the ultraviolet absorber.

Further, the first ultraviolet absorber has a wavelength of a highest absorption maximum more than that of the second ultraviolet absorber. Specifically, the highest absorption maximum thereof is preferably in a wavelength region of 375 nm or more and less than 400 nm, and more preferably in a wavelength region of 380 to 395 nm.

The content of the first ultraviolet absorber may be adjusted such that the maximum transmittance in a specific wavelength and the ratio of the transmittance are within a predetermined range, and is, for example, 0.001 to 0.4% by mass based on the total amount of the ultraviolet absorbing layer. The suitable values of the contents vary depending on the kinds of compounds used for the ultraviolet absorber. The specific values therefor have been described above.

The wavelength of the highest absorption maximum can be measured according to the following procedure. The ultraviolet absorber of which the highest absorption maximum is to be measured is mixed with acetone, to obtain a measurement sample. In the latter measurement of the wavelength of the highest absorption maximum using a spectral photometer, the concentration of the measurement sample is appropriately adjusted such that the transmittance at the wavelength of the highest absorption maximum is set to 40 to 50%. The obtained measurement sample is placed in a quartz cell of a 1 cm square, and a transmittance at a wavelength of 300 to 400 nm is measured at 20° C. using a spectral photometer ("U-4100", manufactured by Hitachi High-Technologies Corporation). The wavelength at which the transmittance is the lowest in the range of the wavelength of 300 to 400 nm is taken as the wavelength of the highest absorption maximum of the ultraviolet absorber.

Examples of the second ultraviolet absorber include a compound having a highest absorption maximum in a wavelength region of, for example, 330 to 380 nm, preferably 330 to 370 nm, and more preferably 347.5 to 360 nm. Specific preferable examples thereof include a triazine-based compound, a benzotriazole-based compound, and a benzophenone-based compound. A benzotriazole-based compound is more preferable.

The content of the second ultraviolet absorber may be adjusted such that the maximum transmittance at a specific wavelength and the ratio of the transmittance are set to be within a predetermined range. The content of the second ultraviolet absorber is, for example, 5% by mass or less, and preferably 0.1 to 1.5% by mass, based on the total amount of the ultraviolet absorbing layer. When the content is set to 0.1% by mass or more, the maximum transmittance in a wavelength region of 370 nm or more and 400 nm or less is likely to be reduced. The content is set to 1.5% by mass or less, whereby the coloring of the ultraviolet absorbing layer caused by the ultraviolet absorber can be prevented. Furthermore, blooming (deposition in powder form on the surface) of the ultraviolet absorber from the intermediate film, and a decreased transmittance in a visible light range can be prevented.

The content of the second ultraviolet absorber is more preferably 0.2% by mass or more, still more preferably 0.3% by mass or more, and particularly preferably 0.5% by mass or more. The content is more preferably 1.2% by mass or less, still more preferably 1.0% by mass or less, and yet still more preferably 0.8% by mass or less.

Examples of the benzotriazole-based compound used for the second ultraviolet absorber include a compound represented by the following formula (3),

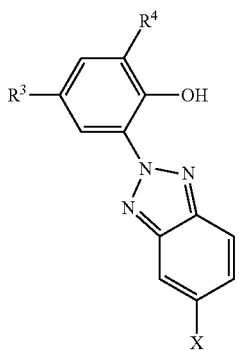

(3)

wherein R³ represents a hydrogen atom, an alkyl group having 1 to 8 carbon atoms, or an alkoxycarbonylalkyl group having 4 to 20 carbon atoms; R⁴ represents a hydrogen atom or an alkyl group having 1 to 8 carbon atoms; and X is a chlorine atom or a hydrogen atom.

In the formula (3), the alkyl groups of R³ and R⁴ may have a straight chain structure or a branched structure. The alkoxycarbonylalkyl group may have a straight chain structure or a branched structure. Examples of R³ and R⁴ include a hydrogen atom, methyl, ethyl, n-propyl, iso-propyl, n-butyl, tert-butyl, pentyl, hexyl, and octyl groups. Examples of R³ include, in addition to these groups, methoxycarbonylpropyl and octyloxycarbonylpropyl groups. Among these, R³ is preferably a hydrogen atom or an alkyl group, and particularly preferably a hydrogen atom, and methyl, tert-butyl, pentyl, and octyl groups. R³ may be the same as or different from R⁴.

Specific examples of the compound represented by the formula (3) include 2-(3-t-butyl-5-methyl-2-hydroxyphenyl)-5-chlorobenzotriazole, 2-(3,5-di-t-butyl-2-hydroxyphenyl)-5-chlorobenzotriazole, 3-[3-tert-butyl-5-(5-chloro-2H-benzotriazole-2-yl)-4-hydroxyphenyl]octyl propionate, 3-(5-chloro-2H-benzotriazole-2-yl)-5-(1,1-dimethylethyl)-4-hydroxyphenyl methyl propionate, and 2-(3, 5-di-tert-amyl-2-hydroxyphenyl)benzotriazole.

Furthermore, the benzotriazole-based compound used for the second ultraviolet absorber may be a commercially available product. Examples thereof include TINUVIN 326 and TINUVIN 327 (trade name, manufactured by Ciba Specially Chemicals Inc.), and Eversorb 109 and Eversorb 88 (trade name, manufactured by Everlight Chemical).

Furthermore, examples of the triazine-based compound include known compounds having a triazine skeleton and used as the ultraviolet absorber.

Specific examples of the triazine-based compound include hydroxyphenyl triazine-based compounds typified by TINUVIN460 and TINUVIN477 (trade name, manufactured by Ciba Specialty Chemicals Inc.).

The ultraviolet absorbing layer preferably comprises the thermoplastic resin, as described above. The ultraviolet absorbing layer comprises the thermoplastic resin, which is likely to serve a function as the adhesion layer, whereby the light control body can be easily bonded to glass. Examples of the thermoplastic resin include, but are not particularly limited to, a polyvinyl acetal resin, an ethylene-vinyl acetate copolymer resin, and an ionomer resin. The use of these resins is likely to secure adhesiveness with the glass plate. In the ultraviolet absorbing layer, each of the thermoplastic resins may be used alone, or two or more of them may be used in combination. Among these, a polyvinyl acetal resin is suitable from the viewpoint of exhibiting excellent adhesiveness to glass in the case when the polyvinyl acetal resin is used in combination with a plasticizer.

In the glass structure of the present invention, as described above, preferably, the adhesion layer (second adhesion layer) is provided between the second glass plate and the light control body, and the light control body is bonded to the second glass plate with the second adhesion layer interposed therebetween. The second adhesion layer is a layer comprising the thermoplastic resin and it can easily bond the second glass plate and the light control body to each other with the thermoplastic resin.

Examples of the thermoplastic resin used for the second adhesion layer include, but are not particularly limited to, a polyvinyl acetal resin, an ethylene-vinyl acetate copolymer resin, and an ionomer resin. The use of these resins is likely to secure adhesiveness with the glass plate. In the second adhesion layer, each of the thermoplastic resins may be used alone, or two or more of them may be used in combination. The thermoplastic resin used for the second adhesion layer is preferably a polyvinyl acetal resin.

The thermoplastic resin used for the second adhesion layer may be the same as or different from the thermoplastic resin used for the ultraviolet absorbing layer (first adhesion layer).

The second adhesion layer preferably has a higher visible light transmittance as with the ultraviolet absorbing layer. Specifically, the visible light transmittance thereof is preferably 70% or more, more preferably 80% or more, and still more preferably 85% or more.

(Polyvinyl Acetal Resin)

The polyvinyl acetal resin used for the ultraviolet absorbing layer and the second adhesion layer is not particularly limited as long as it is obtained by acetalizing a polyvinyl alcohol with an aldehyde, and a polyvinyl butyral resin is suitable.

A preferable lower limit of the acetalization degree of the polyvinyl acetal resin is 40 mol %, and a preferable upper limit thereof is 85 mol %. Amore preferable lower limit thereof is 60 mol %, and a more preferable upper limit thereof is 75 mol %.

A preferable lower limit of the amount of hydroxyl groups of the polyvinyl acetal resin is 15 mol %, and a preferable upper limit thereof is 35 mol %. The amount of the hydroxyl groups of 15 mol % or more is likely to provide good adhesiveness between the glass plate and the ultraviolet absorbing layer or the second adhesion layer, and good penetration resistance of the glass structure, and the like. Further, the amount of the hydroxyl groups is set to 35 mol % or less, which prevents the glass structure from being too hard. A more preferable lower limit of the amount of the hydroxyl groups is 25 mol %, and a more preferable upper limit thereof is 33 mol %.

In the case when a polyvinyl butyral resin is used as the polyvinyl acetal resin, from the same viewpoint, a preferable lower limit of the amount of the hydroxyl groups is 15 mol %, and a preferable upper limit thereof is 35 mol %. A more preferable lower limit of the hydroxyl groups is 25 mol %, and a more preferable upper limit thereof is 33 mol %.

The acetalization degree and the amount of the hydroxyl groups can be measured by a method based on JIS K 6728 "Testing methods for polyvinyl butyral", for example.

The polyvinyl acetal resin can be prepared by acetalizing a polyvinyl alcohol with an aldehyde. The polyvinyl alcohol is typically obtained by saponifying a poly vinyl acetate, and a polyvinyl alcohol with a saponification degree of 80 to 99.8 mol % is generally used.

A preferable lower limit of the polymerization degree of the polyvinyl acetal resin is 500, and a preferable upper limit thereof is 4,000. The polymerization degree is set to 500 or more, whereby the glass structure has good penetration resistance. The polymerization degree is set to 4,000 or less, whereby the glass structure is likely to be molded with ease. A preferable lower limit of the polymerization degree is 1000, and a preferable upper limit thereof is 3600.

The aldehyde is not particularly limited, and generally, an aldehyde with carbon atoms of 1 to 10 is suitably used. The aldehyde with carbon atoms of 1 to 10 is not particularly limited, and examples thereof include n-butyl aldehyde, isobutyl aldehyde, n-valeraldehyde, 2-ethyl butyl aldehyde, n-hexyl aldehyde, n-octyl aldehyde, n-nonyl aldehyde, n-decyl aldehyde, formaldehyde, acetaldehyde, and benzaldehyde. Among these, n-butyl aldehyde, n-hexyl aldehyde, and n-valeraldehyde are preferable, and n-butyl aldehyde is more preferable. Each of these aldehydes may be used alone, or two or more of them may be used in combination.

(Ethylene-Vinyl Acetate Copolymer Resin)

The ethylene-vinyl acetate copolymer resin used for the ultraviolet absorbing layer and the second adhesion layer may be a non-crosslinkable type ethylene-vinyl acetate copolymer resin or a high temperature crosslinkable type ethylene-vinyl acetate copolymer resin. There may also be used modified ethylene-vinyl acetate resins such as saponified ethylene-vinyl acetate copolymer and hydrolyzed ethylene vinyl acetate as the ethylene-vinyl acetate copolymer resin.

In each of the ultraviolet absorbing layer and the second adhesion layer, the ethylene-vinyl acetate copolymer resin preferably has a vinyl acetate content of 10 to 50% by mass, and more preferably 20 to 40% by mass, as measured based on JIS K 6730 "Testing method for ethylene-vinyl acetate resin". The vinyl acetate content is set to be equal to or greater than these lower limits, whereby the adhesiveness between the ultraviolet absorbing layer or the second adhesion layer and the glass, and the penetration resistance of the glass structure are likely to be good. The vinyl acetate content is set to be equal to or less than these upper limits, whereby the breaking strength of the ultraviolet absorbing layer or the second adhesion layer is increased, which provides good shock resistance of the glass structure.

(Ionomer Resin)

The ionomer resin is not particularly limited, and various ionomer resins may be used. Specific examples thereof include an ethylene-based ionomer, a styrene-based ionomer, a perfluorocarbon-based ionomer, a telechelic ionomer, and a polyurethane ionomer. Among these ionomers, an ethylene-based ionomer is preferable from the viewpoints of good mechanical strength, endurance, and transparency and the like of the glass structure, and excellent adhesiveness to glass.

Since an ionomer of an ethylene-unsaturated carboxylic acid copolymer has excellent transparency and high toughness, the ionomer is suitably used as the ethylene-based ionomer. The ethylene-unsaturated carboxylic acid copolymer is a copolymer comprising at least a constitutional unit derived from ethylene and a constitutional unit derived from unsaturated carboxylic acid, and may have a constitutional unit derived from other monomer.

Examples of the unsaturated carboxylic acid include acrylic acid, methacrylic acid, and maleic acid. Acrylic acid and methacrylic acid are preferable, and methacrylic acid is particularly preferable. Examples of the other monomer include an acrylic acid ester, a methacrylic acid ester, and 1-butene.

The ethylene-unsaturated carboxylic acid copolymer preferably comprises 75 to 99 mol % of the constitutional unit derived from ethylene when all the constitutional units comprised in the copolymer is 100 mol %, and preferably comprises 1 to 25 mol % of the constitutional unit derived from unsaturated carboxylic acid.

The ionomer of the ethylene-unsaturated carboxylic acid copolymer is an ionomer resin obtained by neutralizing or crosslinking at least a part of carboxyl groups contained in the ethylene-unsaturated carboxylic acid copolymer with metal ions. The degree of neutralization of the carboxyl group is generally 1 to 90%, and preferably 5 to 85%.

Examples of an ion source in the ionomer resin include alkaline metals such as lithium, sodium, potassium, rubidium, and cesium, and polyvalent metals such as magnesium, calcium, and zinc. Sodium and zinc are preferable.

A method for manufacturing the ionomer resin is not particularly limited, and the ionomer resin can be manufactured by a conventionally known manufacturing method. For example, when the ionomer of ethylene-unsaturated carboxylic acid copolymer is used as the ionomer resin, for example, ethylene and unsaturated carboxylic acid are subjected to radical copolymerization under an elevated temperature and pressure condition to manufacture an ethylene-unsaturated carboxylic acid copolymer. The ionomer of ethylene-unsaturated carboxylic acid copolymer can be manufactured by causing the ethylene-unsaturated carboxylic acid copolymer to react with a metallic compound containing the ion source.

(Plasticizer)

The ultraviolet absorbing layer may further comprise a plasticizer in the case when it comprises the thermoplastic resin. The second adhesion layer may also comprise a plasticizer in addition to the thermoplastic resin. The ultraviolet absorbing layer and the second adhesion layer comprise the plasticizer, whereby the ultraviolet absorbing layer and the second adhesion layer are flexible. As a result, the glass structure is flexible. Furthermore, high adhesiveness to the glass plate can also be exhibited. When the polyvinyl acetal resin is used as the thermoplastic resin of the ultraviolet absorbing layer and the second adhesion layer, the plasticizer comprised in the layers is particularly effective.

Examples of the plasticizer include triethylene glycol di-2-ethyl butyrate; triethylene glycol di-2-ethylhexanoate; triethylene glycol dicaprylate; triethylene glycol di-n-octanoate; triethylene glycol di-n-heptanoate; tetraethylene glycol di-n-heptanoate; tetraethylene glycol di-2-ethylhexanoate; dibutyl sebacate; dioctyl azelate; dibutyl carbitol adipate; ethylene glycol di-2-ethyl butyrate; 1,3-propylene glycol di-2-ethylbutyrate; 1,4-butylene glycol di-2-ethylbutyrate; 1,2-butylene glycol di-2-ethylbutyrate; diethylene glycol di-2-ethylbutyrate; diethylene glycol di-2-ethylhexanoate; dipropylene glycol di-2-ethylbutyrate; triethylene glycol di-2-ethylpentanoate; tetraethylene glycol di-2-ethylbutyrate; diethylene glycol dicapriate; triethylene glycol di-n-heptanoate; tetraethylene glycol di-n-heptanoate; triethylene glycol di-2-ethyl butyrate; adipic acid dihexyl; adipic acid dioctyl; hexylcyclohexyl adipate; diisononyl adipate; heptyl nonyl adipate; dibutyl sebacate; oil-modified alkyd sebacate; mixtures of a phosphoric acid ester and an adipic acid ester; mixed adipic acid esters produced from an adipic acid ester, an alkyl alcohol having 4 to 9 carbon atoms, and a cyclic alcohol having 4 to 9 carbon atoms; and adipic acid esters having 6 to 8 carbon atoms such as adipic acid hexyl. Each of the plasticizers may be used alone, or two or more of them may be used in combination. Among these plasticizers, triethylene glycol-di-2-ethylhexanoate (3GO) is particularly suitably used.

In each of the ultraviolet absorbing layer and the second adhesion layer, the content of the plasticizer is not particularly limited, and a preferable lower limit of the content thereof is 30 parts by mass, and a preferable upper limit thereof is 70 parts by mass, per 100 parts by mass of the thermoplastic resin. If the content of the plasticizer is 30 parts by mass or more, the glass structure is moderately flexible, which provides good handleability and the like. If the content of the plasticizer is 70 parts by mass or less, the plasticizer is prevented from being separated from the ultraviolet absorbing layer. A preferable lower limit of the content of the plasticizer is 35 parts by mass, and a preferable upper limit thereof is 63 parts by mass.

In the case when each of the ultraviolet absorbing layer and the second adhesion layer of the present invention comprises the thermoplastic resin, each of the layers comprises the thermoplastic resin, or the thermoplastic resin and the plasticizer as a main component. The total amount of the thermoplastic resin and the plasticizer is typically 70% by mass or more, preferably 80% by mass or more, and still more preferably 90% by mass or more, based on the total amount of the ultraviolet absorbing layer (or the second adhesion layer).

The second adhesion layer may comprise an ultraviolet absorber. The second adhesion layer may have the same configuration as that of the ultraviolet absorbing layer: the second adhesion layer has a maximum transmittance of 10% or less in a wavelength region of 370 nm or more and 400 nm or less and a maximum transmittance of 50% or more in a wavelength region of more than 400 nm and 420 nm or less, and a ratio of a transmittance at 405 nm to a transmittance at 395 nm is 12 or more. Such optical characteristics can be obtained by adding the ultraviolet absorber to the second adhesion layer.

The second adhesion layer has such optical characteristics, whereby the deterioration of the light control body can be suitably prevented even if the second glass plate side is an outdoor side, and sunlight is made incident into the glass structure from the second glass plate side. Therefore, even if any of the first and second glass plates is disposed on the outdoor side, the effect of the present invention is obtained, which provides reduced restrictions when the glass structure is incorporated into automobiles and buildings and the like. Even when sunlight is made incident from both the first and second glass plates, the deterioration of the light control body can be prevented.

The second adhesion layer preferably has a maximum transmittance of 7% or less in a wavelength region of 370 nm or more and 400 nm or less, and more preferably 5% or less. The maximum transmittance in a wavelength region of 370 nm or more and 400 nm or less is preferably lower, and it is practically preferably 0.1% or more, and more preferably 0.5% or more.

The second adhesion layer preferably has a maximum transmittance of 60% or more in a wavelength region of more than 400 nm and 420 nm or less, and more preferably 70% or more. The maximum transmittance in a wavelength region of more than 400 nm and 420 nm or less is preferably higher, and an upper limit thereof is 100%.

In the second adhesion layer, the ratio of a transmittance of 405 nm to a transmittance at 395 nm is preferably 15 or more, more preferably 17 or more, and still more preferably 20 or more. The ratio of the transmittance is preferably higher. The ratio of the transmittance is practically preferably 400 or less, and more preferably 200 or less. The ratio of the transmittance is still more preferably 50 or less.

The details and content and the like of the ultraviolet absorber in the second adhesion layer for having the optical characteristics have been described in the ultraviolet absorber in the ultraviolet absorbing layer, and the descriptions thereof are omitted. The ultraviolet absorber used for the second adhesion layer in the glass structure may be the same as or different from the ultraviolet absorber used for the ultraviolet absorbing layer. The content of each ultraviolet absorber of the second adhesion layer may be the same as or different from the content of each ultraviolet absorber in the ultraviolet absorbing layer. Furthermore, in the case when at least two ultraviolet absorbers (first and second ultraviolet absorbers) are used in the ultraviolet absorbing layer, only the second ultraviolet absorber may be blended in the second adhesion layer without blending the first ultraviolet absorber, for example.

(Other Additives)

Each of the ultraviolet absorbing layer and the second adhesion layer may further comprise an infrared absorbing agent. Each of the ultraviolet absorbing layer and the second adhesion layer comprising the infrared absorbing agent can exhibit high heat insulation. The infrared absorbing agent is not particularly limited as long as it has the property of shielding infrared rays, and suitable examples thereof include tin-doped indium oxide particles.

Each of the ultraviolet absorbing layer and the second adhesion layer may further comprise additives such as an antioxidant, a light stabilizer, an adhesion control agent, a colorant, a dye, a fluorescent whitening agent, and a nucleating agent as necessary.

The antioxidant is not particularly limited, and examples thereof include 2,2-bis[[[3-(3,5-di-tert-butyl-4-hydroxyphenyl)propionyl]oxy]methyl]propane-1,3-diol1,3-bis[3-(3,5-di-tert-butyl-4-hydroxyphenyl)propionate], 4,4'-thiobis(6-tert-butyl-3-methylphenol), 4,4'-dimethyl-6,6'-di(tert-butyl) [2,2'-methylenebis(phenol)], 2,6-di-t-butyl-p-cresol, and 4,4'-butylidenebis-(6-t-butyl-3-methylphenol).

The nucleating agent is not particularly limited, and examples thereof include dibenzylidene sorbitol, dibenzylidene xylitol, dibenzylidene dulcitol, dibenzylidene mannitol, and calixarene. In the case when the ethylene-vinyl acetate copolymer resin is used as the thermoplastic resin, the nucleating agent is suitably used.

[Light Control Body]

The light control body of the present invention is a sheet shaped or layer-shaped member in which optical characteristics such as a transmittance at a predetermined wavelength are changed when various energies such as light energy, electric energy, and thermal energy are applied to the member. The light control body preferably has optical characteristics changed by applying electric energy. Specifically, the light control body preferably includes any of a liquid crystal layer and an electrochromic layer.

(Liquid Crystal Layer)

The liquid crystal layer is a layer containing a liquid crystal, and examples thereof include one in which a liquid crystal is filled and sealed in a space formed by a spacer and the like. The liquid crystal may have any type, and may have a TN type or an STN type. The liquid crystal layer may be constituted by a polymer-dispersed liquid crystal (PDLC). Examples of the polymer-dispersed liquid crystal include a so-called network liquid crystal in which a polymer network structure is formed in a liquid crystal layer. The polymer-dispersed liquid crystal may be a microcapsule type liquid crystal (PDMLC) in which a liquid crystal is microencapsulated and dispersed in a binder resin. Examples of the binder resin used in PDMLC include a polyvinyl acetal resin such as a polyvinyl butyral resin.

The light control body includes a pair of transparent electrodes, for example, and a liquid crystal layer is disposed between the transparent electrodes to constitute a liquid crystal cell. An oriented film and the like may be provided between an electrode and a liquid crystal layer depending on the kind of the liquid crystal. In the PDLC and the PDMLC and the like, the oriented film is unnecessary. When a voltage is applied between the transparent electrodes, the liquid crystal in the liquid crystal layer is oriented in a single direction to cause light to transmit in the thickness direction of the light control body. Therefore, when the light control body includes the liquid crystal layer, the optical transmittances of the light control body and the glass structure including the light control body are increased by applying a voltage, which provides a transparent light control body and glass structure. Meanwhile, when a voltage is not applied, the optical transmittances of the light control body and the glass structure including the light control body are decreased, which provides an opaque light control body and glass structure, for example.

(Electrochromic Layer)

The electrochromic layer is a layer composed of an electrochromic material. The electrochromic material is not limited as long as it is a compound having electrochromic properties. The electrochromic material may be any of an inorganic compound, an organic compound, and a mixed valence complex.

Examples of the inorganic compound include $Mo_2O_3$, $Ir_2O_3$, NiO, $V_2O_5$, $WO_3$, and $TiO_2$. Examples of the organic compound include a polypyrrole compound, a polythiophene compound, a polyparaphenylene vinylene compound, a polyaniline compound, a polyacetylene compound, a polyethylene dioxythiophene compound, a metal phthalocyanine compound, a viologen compound, a viologen salt compound, a ferrocene compound, a dimethyl terephthalate compound, and a diethyl terephthalate compound. Among these, a polyacetylene compound is preferable. Examples of the mixed valence complex include a Prussian blue type complex ($KFe[Fe(CN)_6]$ and the like).

The electrochromic layer can be formed by known methods, may be formed by sputtering, or may be formed by applying a solution in which an electrochromic material is diluted.

In the case when the light control body includes the electrochromic layer, the light control body may include a pair of transparent electrodes and the electrochromic layer disposed between the transparent electrodes. By applying a voltage between the transparent electrodes in the electrochromic layer, for example, a transmittance in a specific wavelength region is changed, whereby the transparent light control body is changed to an opaque light control body, or a color tone when irradiated with visible light is changed. Therefore, for example, when a voltage is not applied, the light control body is colorless and transparent, by contrast, when a voltage is applied, the light control body can have color tones such as blue, yellow, green, and red.

Between the transparent electrode and the electrochromic layer, various layers used in combination with the electrochromic layer such as an electrolyte layer may be provided. The electrolyte layer may contain a substance having thermochromic properties in which a transmittance in a predetermined region is changed in response to heat and the like as necessary. The light control body comprises the substance having thermochromic properties, whereby the transmittance in a specific wavelength region can be changed by heating and cooling.

The light control body generally includes a pair of substrates composed of a resin film and the like, and the pair of transparent electrodes and the electrochromic layer or the liquid crystal layer are disposed between the pair of the substrates. One resin film may be omitted in the light control body; one transparent electrode may be directly provided on the second glass; and the second adhesion layer may be omitted.

In the present invention, as described above, when energy is applied or is not applied to the light control body by voltage application and the like, the light control body has a high transmittance, and is transparent. When such a high transmittance is achieved, a visible light transmittance is 70% or more, more preferably 80% or more, and still more preferably 90% or more. Thus, the high visible light transmittance of the light control body is likely to provide good light permeability of the whole glass structure

[Glass Plate]

The glass plates (first and second glass plates) of the present invention are not particularly limited, and transparent glass plates for general use may be used. Examples thereof include clear glass, float plate glass, polished plate glass, figured glass, net-wired plate glass, line-wired plate glass, infrared absorbing plate glass, infrared reflective plate glass, and green glass.

(Thicknesses of Layers)

In the present invention, the ratio of the thickness of the light control body to that of the ultraviolet absorbing layer is preferably 0.5 to 10.5. The ratio of the thickness is set to 10.5 or less, whereby the transmittance in a long-wavelength ultraviolet region (370 to 400 nm) can be set to a desired value even when the content rate of the ultraviolet absorber is not increased. The ratio of the thickness is set to 0.5 or more, whereby the ultraviolet absorbing layer is prevented from increasing in thickness more than necessary, which is likely to provide improved transparency of the glass structure.

Furthermore, in the case when the ultraviolet absorbing layer comprises the thermoplastic resin, the thickness is set to be within the above range, which makes it possible to cause the ultraviolet absorbing layer to suitably bond the light control body to the first glass plate, and provides improved penetration resistance and the like of the glass structure. The ratio of the thickness is more preferably 0.6 to 5.0.

The ratio of the thickness of the light control body to that of the second adhesion layer is preferably 0.5 to 10.5. The ratio of the thickness is set to be within the above range, whereby the second adhesion layer is prevented from increasing in thickness more than necessary, which is likely to provide improved transparency of the glass structure. This makes it possible to cause the second adhesion layer to suitably bond the light control body to the second glass plate, and provide improved penetration resistance and the like of the glass structure. From these viewpoints, the ratio of the thickness of the light control body to that of the second adhesion layer is more preferably 0.6 to 5.0.

The thicknesses of the ultraviolet absorbing layer, second adhesion layer, and light control body may be appropriately adjusted such that the ratio of the thickness is set to be within the above range. The thickness of the ultraviolet absorbing layer is preferably 0.05 to 1.5 mm, more preferably 0.1 to 1 mm, and still more preferably 0.2 to 0.6 mm. The thickness of the second adhesion layer is preferably 0.05 to 1.5 mm, more preferably 0.1 to 1 mm, and still more preferably 0.2 to 0.6 mm. The thickness of the second adhesion layer may be the same as or different from the thickness of the ultraviolet absorbing layer.

Further, the thickness of the light control body is preferably 0.1 to 4 mm, more preferably 0.2 to 1.5 mm, and still more preferably 0.3 to 1.5 mm.

Furthermore, the thickness of the glass plate is not particularly limited, and it is, for example, about 0.1 to 15 mm, and preferably 0.5 to 5 mm.

The glass structure of the present invention preferably has a visible light transmittance of 55% or more. When the visible light transmittance is set to 55% or more, the glass structure can secure comparably high transparency, compared to that of laminated glass including no light control body. The visible light transmittance of the glass structure is more preferably 65% or more, and still more preferably 70% or more. The visible light transmittance of the glass structure may be within these ranges when the transmittance is high as well as the case of the light control body.

[Uses of Glass Structure]

The glass structure of the present invention is preferably used in an application in which one surface of the glass structure is disposed on an outdoor side into which sunlight is made incident. In such an application, usually, the first glass plate side may be the outdoor side. When the second adhesion layer has the predetermined optical characteristics (the maximum transmittance and the ratio of the transmittance), the second glass plate side may be the outdoor side.

The glass structure of the present invention can be used in various fields, and is preferably used for various vehicles such as automobiles, trains, and vessels, and outdoor windows for various constructions such as buildings, condominiums, stand-alone houses, halls, and gymnasiums. Herein, the outdoor window means a window disposed at a position into which sunlight is made incident. Therefore, the outdoor window is usually disposed on the external surface of a building, and the external surface of a vehicle, and an inner window of a double window is also included in the outdoor window herein even if the inner window is disposed at the position into which sunlight is made incident.

The glass structure is preferably used for a rear window, a side window, and a roof window in an automobile, and particularly preferably used for a roof window. When the glass structure is used for these applications, the glass structure does not inhibit a field of view during driving even if the application of a voltage and the like causes the opaque glass structure, and can be suitably used.

[Method for Manufacturing Glass Structure]

The glass structure of the present invention may be manufactured by disposing at least the ultraviolet absorbing layer and the light control body between the two glass plates (first and second glass plates), and pressure-bonding them for integrating. In such a case, when the glass structure further includes the second adhesion layer, the glass structure may be manufactured by disposing the ultraviolet absorbing layer, the light control body, and the second adhesion layer in this order between the two glass plates, and pressure-bonding them for integrating.

Further, when the second adhesion layer is omitted, the glass structure may be manufactured by first forming the light control body on the second glass plate, stacking the second glass plate, the ultraviolet absorbing layer, and the first glass plate, and pressure-bonding them.

The glass structure may be manufactured by forming the ultraviolet absorbing layer on the first glass plate, stacking the first glass plate, the light control body, the second glass plate or the first glass plate, the light control body, the second adhesion layer, and the second glass plate, and pressure-bonding them.

Each of the ultraviolet absorbing layer and the second adhesion layer may be molded by, for example, kneading materials constituting the layers such as a thermoplastic resin and an ultraviolet absorber, and subjecting the obtained composition to extrusion molding or press molding. When the plasticizer is used at this time, the composition may be produced by dissolving the ultraviolet absorber in the plasticizer to obtain a mixture, and kneading the mixture and the thermoplastic resin such as a polyvinyl acetal resin.

In the case when the ultraviolet absorbing layer does not contain the thermoplastic resin, the materials constituting the ultraviolet absorbing layer such as the ultraviolet absorber may be applied to the first glass plate and the like to form the ultraviolet absorbing layer.

EXAMPLES

The present invention will be described in further detail by referring to Examples, but the present invention is by no means limited by these examples.

[Maximum Transmittance and Ratio of Transmittance]

In the following (4) Production of Glass structure, a light control body and a second adhesion layer were excluded, and the transmittance of a glass structure produced according to the following (4) Production of Glass structure was measured using a spectral photometer ("U-4100", manufactured by Hitachi High-Technologies Corporation). The transmittance of an ultraviolet absorbing layer was calculated by deducting the transmittance of a clear glass having a thickness of 2.5 mm. A clear glass based on JIS R 3202 in measurement of each transmittance was used. The transmittance was measured per 1 nm, and a maximum transmittance in a wavelength region of 370 nm or more and 400 nm or less and a maximum transmittance in a wavelength region of more than 400 nm and 420 nm or less were obtained. The ratio of a transmittance at 405 nm to a transmittance at 395 nm was also obtained.

[Visible Light Transmittance]

The visible light transmittances of the ultraviolet absorbing layer, glass structure, and light control body were measured using a spectral photometer ("U-4100", manufactured by Hitachi High-Technologies Corporation) based on JIS R 3106 (1998).

[Light Resistance]

The glass structure was irradiated with ultraviolet rays for 5000 hours using an ultraviolet ray irradiation device from the side of a first glass plate based on JIS R 3205 (1998) to measure ΔE (color difference) before and after the ultraviolet ray irradiation. ΔE was measured using a spectral photometer ("U-4100", manufactured by Hitachi High-Technologies Corporation) based on JIS K 8781-4 (2013) to obtain ΔE (color difference). SX-70 manufactured by Suga Test Instruments Co., Ltd. was used as the ultraviolet ray irradiation device. An ultraviolet irradiation condition included a black panel temperature of 63° C., a temperature in a bath of 50° C., a humidity in a bath of 50% $R^{11}$, irradiance of 60 W/m$^2$, and an irradiance measurement wavelength of 300 to 400 nm. An inner filter made of quartz and an outer filter made of #275 quartz were used.

[Penetration Resistance]

The state of the glass structure was adjusted in a constant temperature/constant humidity dark room having a relative humidity of 50% at 23° C. for 48 hours. Then, a rigid sphere having a mass of 2260 g and a diameter of 82 mm was dropped onto laminated glass from a height of 5 m based on JIS R 3212 (1998) "Test method of safety glass for automobiles"), to confirm whether the rigid sphere penetrated within 5 seconds after impact. A case where the rigid sphere did not penetrate was taken as A, and a case where the rigid sphere penetrated was taken as B.

Compounds used for the ultraviolet absorbing layer in each of Examples and Comparative Examples are as follows.

(1) First Ultraviolet Absorber
Indole-Based Compound:
To methanol (120 ml), 23.5 g (0.10 mol) of 1-methyl-2-phenyl-1H-indole-3-carbaldehyde and 11.9 g (0.12 mol) of methyl cyanoacetate were added. Then, 2.5 g (0.03 mol) of piperidine was added thereto. The mixture was reacted for 6 hours with reflux and then cooled to room temperature. Thereby, a precipitated crystal was obtained. The obtained crystal was washed with a small amount of alcohol, and then dried to obtain 30.9 g of a pale yellow crystal of an indole-based compound, in which $R^1$ was a methyl group and $R^2$ was a methyl group in the formula (1). The obtained indole compound had a melting point of 193.7° C. and a highest absorption maximum of 391 nm.

Benzotriazole-based compound (1): TINUVIN CarboProtect (trade name, manufactured by BASF A.G.), compound name: "6-butyl-2-[2-hydroxy-3-(1-methyl-1-phenylethyl)-5-(1, 1,3,3-tetramethylbutyl)-phenyl]-pyrrolo[3,4-f][benzotriazole-5,7(2H,6H)-dione]", highest absorption maximum of 380 nm Coumarin-based compound: Eusorb UV-1990 (trade name, manufactured by Eutec Chemical Co., Ltd.), highest absorption maximum of 384 nm (2) Other Compounds
Polyvinyl butyral resin: acetalization degree of 69 mol %, amount of hydroxyl groups of 30 mol %, acetylation degree of 1 mol %, polymerization degree of 1700

Plasticizer: triethylene glycol di-2-ethylhexanoate (3GO)
Antioxidant: 2, 6-di-t-butyl-p-cresol (BHT)
Benzotriazole-based compound (2): benzotriazole-based compound satisfying the formula (3) (X: chlorine atom, $R^3$: methyl group, $R^4$: tert-butyl group), trade name: Tinuvin 326, manufactured by Ciba Specialty Chemicals Inc., highest absorption maximum: 353 nm Benzotriazole-based compound (3): benzotriazole-based compound satisfying the formula (3) (X: chlorine atom, $R^3$: alkoxycarbonylalkyl group represented by —$CH_2CH_2$—COO—$C_8H_7$, $R^4$: tert-butyl group), trade name: Eversorb 109, manufactured by Everlight Chemical, highest absorption maximum: 350 nm Benzotriazole-based compound (4): benzotriazole-based compound satisfying the formula (3) (X: chlorine atom, $R^3$: alkoxycarbonylalkyl group represented by —$CH_2CH_2$—COO—$CH_3$, $R^4$: tert-butyl group, trade name: Eversorb 88, manufactured by Everlight Chemical, highest absorption maximum: 352.5 nm Benzotriazole-based compound (5): 2-(4-butoxy-2-hydroxyphenyl)-2H-benzotriazole, trade name: DAINSORB T-53, manufactured by Daiwa Kasei Industry Co., Ltd., highest absorption maximum: 345 nm TINUVIN 1600 (trade name: manufactured by BASF A.G., highest absorption maximum: 320 nm)

Ethylene-vinyl acetate copolymer resin: vinyl acetate content: 28% by mass Infrared absorbing agent: tin-doped indium oxide particles (hereinafter, may be referred to simply as ITO)

Example 1

(1) Production of Ultraviolet Absorbing Layer
A polyvinyl butyral resin (PVB), a plasticizer, an antioxidant, an indole-based compound as a first ultraviolet absorber, and a benzotriazole-based compound (2) as a second ultraviolet absorber were mixed such that the contents of the polyvinyl butyral resin, plasticizer, antioxidant, indole-based compound, and benzotriazole-based compound (2) in an ultraviolet absorbing layer were respectively set to 71.21% by mass, 27.93% by mass, 0.14% by mass, 0.01% by mass, and 0.73% by mass. The content of the plasticizer was 39.2 parts by mass relative to 100 parts by mass of the PVB. The mixture was subjected to extrusion molding with a biaxial anisotropic extruder to produce an ultraviolet absorbing layer having a film thickness of 380 μm. When the compounds were mixed, an organic acid magnesium aqueous solution as an adhesion control agent was further added into the mixture such that a Mg concentration in the ultraviolet absorbing layer was set to 65 ppm.

(2) Production of Second Adhesion Layer
Components were mixed in the same proportions, except that 0.01% by mass of an indole-based compound was not contained, to produce a second adhesion layer as with the ultraviolet absorbing layer.

(3) Production of Light Control Body
In a separable flask, 100 parts by mass of toluene, 10 parts by mass of a liquid crystal (chisso Lixon JC5007LA), and 10 parts by mass of polyvinyl butyral having a polymerization degree of 350 were uniformly mixed to prepare a liquid crystal-polyvinyl butyral solution. While the obtained liquid crystal-polyvinyl butyral solution was stirred at 100 rpm, 100 parts by mass of ethanol was dropped into the liquid crystal-polyvinyl butyral solution over 1 hour to obtain a liquid crystal microcapsule dispersion solution.

In a separable flask, 100 parts by mass of toluene, 100 parts by mass of ethanol, 40 parts by mass of polyvinyl butyral having a polymerization degree of 350, and 20 parts by mass of triethylene glycol di-2-ethylhexanoate as a plasticizer were uniformly mixed to prepare a polyvinyl butyral solution. 50 parts by mass of the obtained polyvinyl butyral solution and 100 parts by mass of the liquid crystal microcapsule dispersion solution were mixed to obtain a mixed solution.

The obtained mixed solution was applied onto a polyethylene terephthalate (PET) film subjected to a release treatment with a coater such that the thickness after drying was set to 10 μm, and dried at 120° C. for 10 minutes. A release film was then removed at room temperature to obtain a light control film.

Then, the light control film was interposed between two PET films (substrate) on which an ITO (tin-doped indium oxide) electrode was printed as a transparent electrode, followed by heating and pressure-bonding to obtain a light control body.

(4) Production of Glass Structure
The obtained ultraviolet absorbing layer and second adhesion layer were held under a constant temperature/constant humidity condition of a relative humidity of 28% at 23° C. for 4 hours. Then, two transparent clear glass plates (thickness: 2.5 mm) were prepared. On one of the clear glass plates, the second adhesion layer, the light control body, the ultraviolet absorbing layer, and the other clear glass plate were stacked in this order to obtain a laminated body. The obtained laminated body was placed in a rubber bag. The rubber bag was then connected to a suction decompression system. The rubber bag was heated at an external air heating temperature so that the temperature (preliminary pressure bonding temperature) of the laminated body reached 60° C., while being held under a reduced pressure of −600 mmHg (absolute pressure: 160 mmHg) for 10 minutes. Thereafter, the pressure was returned to atmospheric pressure, whereby the preliminary pressure bonding was performed. The preliminarily pressure-bonded laminated body was held in an autoclave at a temperature of 140° C. and a pressure of 1.3 MPa for 10 minutes. Thereafter, the temperature was lowered to 50° C. and the pressure was returned to atmospheric pressure, whereby the final pressure bonding was completed to produce a glass structure.

A glass structure including a layer constitution of first glass plate/ultraviolet absorbing layer/light control body/second adhesion layer/second glass plate was obtained.

When a voltage was not applied between the transparent electrodes, the light control body and the glass structure were opaque. When a voltage of 12 V was applied, the light control body and the glass structure were transparent.

Example 2

Example 2 was carried out in the same manner as in Example 1, except that an STN liquid crystal cell was used as a light control body. When a voltage was not applied between transparent electrodes, a light control body and a glass structure were opaque. When a voltage of 12 V was applied, the light control body and the glass structure were transparent.

Example 3

An ethylene-vinyl acetate copolymer resin (EVA, vinyl acetate content: 28%), dibenzylidene sorbitol, an indole-based compound as a first ultraviolet absorber, and a benzotriazole-based compound (2) as a second ultraviolet absorber were mixed such that the contents of the ethylene-vinyl acetate copolymer resin, dibenzylidene sorbitol, indole-based compound, and benzotriazole-based compound (2) in an ultraviolet absorbing layer were respectively set to 99.0% by mass, 0.26% by mass, 0.01% by mass, and 0.73% by mass. The mixture was subjected to extrusion molding with a biaxial anisotropic extruder to produce an ultraviolet absorbing layer having a film thickness of 380 µm. Further, components were mixed in the same proportions except that 0.01% by mass of an indole-based compound was not contained, to produce a second adhesion layer as with the ultraviolet absorbing layer.

For a light control body, an electro film as an electrochromic layer obtained by sputtering vanadium oxide in the form of thin film was used. In the electro film, the electrochromic layer was interposed between two PET films in which an ITO electrode as a transparent electrode was printed.

Furthermore, the same clear glass as that of Example 1 was prepared, and a glass structure including a layer constitution of first glass plate/ultraviolet absorbing layer/light control body/second adhesion layer/second glass plate was obtained according to the same technique as that of Example 1.

When a voltage was not applied between the transparent electrodes, the light control body and the glass structure were transparent. When a voltage of 12 V was applied, the light control body and the glass structure were blue.

Example 4

Example 4 was carried out in the same manner as in Example 1, except that an ultraviolet absorbing layer and a second adhesion layer were produced as follows. When a voltage was not applied between transparent electrodes, a light control body and glass structure obtained were opaque. When a voltage of 12 V was applied, the light control body and the glass structure were transparent.

(1) Production of Ultraviolet Absorbing Layer

A polyvinyl butyral resin (PVB), a plasticizer, an antioxidant, a benzotriazole-based compound as a first ultraviolet absorber, and a benzotriazole-based compound (2) as a second ultraviolet absorber were mixed such that the contents of the polyvinyl butyral resin, plasticizer, antioxidant, benzotriazole-based compound (1), and benzotriazole-based compound (2) in an ultraviolet absorbing layer were respectively set to 71.18% by mass, 27.90% by mass, 0.14% by mass, 0.043% by mass, and 0.73% by mass. The content of the plasticizer was 39.2 parts by mass, relative to 100 parts by mass of the PVB. The mixture was subjected to extrusion molding with a biaxial anisotropic extruder to produce an ultraviolet absorbing layer having a film thickness of 380 µm. When the compounds were mixed, an organic acid magnesium aqueous solution as an adhesion control agent was further added into the mixture such that a Mg concentration in the ultraviolet absorbing layer was set to 65 ppm.

(2) Production of Second Adhesion Layer

Components were mixed in the same proportions, except that 0.043% by mass of a benzotriazole-based compound (1) was not contained, to produce a second adhesion layer as with the ultraviolet absorbing layer.

Example 5

Example 5 was carried out in the same manner as in Example 2, except that an ultraviolet absorbing layer and a second adhesion layer were produced as follows. When a voltage was not applied between transparent electrodes, a light control body and glass structure obtained were opaque. When a voltage of 12 V was applied, the light control body and the glass structure were transparent.

(1) Production of Ultraviolet Absorbing Layer

A polyvinyl butyral resin (PVB), a plasticizer, an antioxidant, a coumarin-based compound as a first ultraviolet absorber, and a benzotriazole-based compound (2) as a second ultraviolet absorber were mixed such that the contents of the polyvinyl butyral resin, plasticizer, antioxidant, coumarin-based compound, and benzotriazole-based compound (2) in an ultraviolet absorbing layer were respectively set to 71.2% by mass, 27.91% by mass, 0.14% by mass, 0.014% by mass, and 0.73% by mass. The content of the plasticizer was 39.2 parts by mass, relative to 100 parts by mass of the PVB. The mixture was subjected to extrusion molding with a biaxial anisotropic extruder to produce an ultraviolet absorbing layer having a film thickness of 380 µm. When the compounds were mixed, an organic acid magnesium aqueous solution as an adhesion control agent was further added into the mixture such that a Mg concentration in the ultraviolet absorbing layer was set to 65 ppm.

(2) Production of Second Adhesion Layer

Components were mixed in the same proportions, except that 0.01% by mass of a coumarin-based compound was not contained, to produce a second adhesion layer as with the ultraviolet absorbing layer.

Example 6

Example 6 was carried out in the same manner as in Example 3, except that an ultraviolet absorbing layer and a second adhesion layer were produced as follows. When a voltage was not applied between transparent electrodes, a light control body and glass structure obtained were transparent. When a voltage of 12 V was applied, the light control body and the glass structure were blue.

(1) Production of Ultraviolet Absorbing Layer

An ethylene-vinyl acetate copolymer resin (EVA), dibenzylidene sorbitol, a benzotriazole-based compound (1) as a first ultraviolet absorber, and a benzotriazole-based compound (2) as a second ultraviolet absorber were mixed such that the contents of the ethylene-vinyl acetate copolymer resin, dibenzylidene sorbitol, benzotriazole-based compound (1), and benzotriazole-based compound (2) in an ultraviolet absorbing layer were respectively set to 88.5% by mass, 0.26% by mass, 0.043% by mass, and 0.73% by mass. The mixture was subjected to extrusion molding with a biaxial anisotropic extruder to produce an ultraviolet absorbing layer having a film thickness of 380 µm. The content of vinyl acetate in EVA was 28% by mass.

(2) Production of Second Adhesion Layer

Components were mixed in the same proportions, except that 0.06% by mass of a benzotriazole-based compound (1) was not contained, to produce a second adhesion layer as with the ultraviolet absorbing layer.

Comparative Example 1

A polyvinyl butyral resin, a plasticizer, an antioxidant, and a benzotriazole-based compound (2) as a second ultraviolet absorber were mixed such that the contents of the polyvinyl butyral resin, plasticizer, antioxidant, and benzotriazole-based compound (2) in an ultraviolet absorbing layer were respectively set to 71.4% by mass, 28% by mass (39.2 parts by mass relative to 100 parts by mass of PVB), 0.1% by mass, and 0.5% by mass. The obtained mixture was subjected to extrusion molding with a biaxial anisotropic extruder to produce an ultraviolet absorbing layer having a film thickness of 380 µm. A second adhesion layer was produced in the same manner as that of the ultraviolet absorbing layer.

Furthermore, the same light control body and clear glass as those of Example 1 were prepared, and a glass structure including a layer constitution of first glass plate/ultraviolet absorbing layer/light control body/second adhesion layer/second glass plate was obtained according to the same technique as that of Example 1.

When a voltage was not applied between transparent electrodes, a light control body and a glass structure were opaque. When a voltage of 12 V was applied, the light control body and the glass structure were transparent.

Comparative Example 2

Comparative Example 2 was carried out in the same manner as in Comparative Example 1, except that formulations in an ultraviolet absorbing layer and a second adhesion layer were changed as shown in Table 1.

TABLE 1

| | | | Example 1 | Example 2 | Example 3 | Example 4 | Example 5 | Example 6 | Comparative Example 1 | Comparative Example 2 |
|---|---|---|---|---|---|---|---|---|---|---|
| Thermoplastic resin | Kind | — | PVB | PVB | EVA | PVB | PVB | EVA | PVB | PVB |
| | Content | % | 71.21 | 71.21 | 99 | 71.18 | 71.2 | 99 | 71.4 | 71.4 |
| Plasticizer | Kind | — | 3GO | 3GO | — | 3GO | 3GO | — | 3GO | 3GO |
| | Content | % | 27.6 | 27.6 | — | 27.6 | 27.6 | — | 27.7 | 27.9 |
| Antioxidant | Kind | — | BHT | BHT | — | BHT | BHT | — | BHT | BHT |
| | Content | % | 0.14 | 0.14 | — | 0.14 | 0.14 | — | 0.1 | 0.1 |
| First ultraviolet absorber | Kind | — | Indole | Indole | Indole | Tinuvin Carbo Protect | Coumarin | Tinuvin Carbo Protect | — | — |
| | Content | % | 0.01 | 0.01 | 0.01 | 0.043 | 0.014 | 0.043 | — | — |
| Second ultraviolet absorber | Kind | — | Tinuvin 326 | Tinuvin 326 | Tinuvin 326 | Tinuvin 326 | Tinuvin 326 | Tinuvin 326 | Tinuvin 326 | Tinuvin 326 |
| | Content | % | 0.73 | 0.73 | 0.73 | 0.73 | 0.73 | 0.73 | 0.5 | 0.29 |
| Other additive | Kind | — | — | — | Dibenzylidene sorbitol | — | — | Dibenzylidene sorbitol | — | — |
| | Content | % | — | — | 0.26 | — | — | 0.26 | — | — |
| Light control body | Kind | — | Liquid crystal PVB | STN liquid crystal | $VO_2$ film | Liquid crystal PVB | STN liquid crystal | $VO_2$ film | Liquid crystal PVB | Liquid crystal PVB |
| Power supply OFF | | | Opaque | Opaque | Transparent | Opaque | Opaque | Transparent | Opaque | Opaque |
| Power supply ON | | | Transparent | Transparent | Blue | Transparent | Transparent | Blue | Transparent | Transparent |
| Ultraviolet absorbing layer | Maximum transmittance in 370 or more and 400 nm or less | % | 4.9 | 4.9 | 4.9 | 5.0 | 4.8 | 5.0 | 10.5 | 12.5 |
| | Maximum transmittance in more than 400 nm and 420 nm or less | % | 68.5 | 68.5 | 68.5 | 68.0 | 68.8 | 68.1 | 79.6 | 81.7 |
| | Ratio of transmittance 405 nm/395 nm | % | 17.7 | 17.7 | 17.7 | 17.0 | 18.0 | 17.0 | 10.2 | 15.3 |
| | Visible light transmittance | % | 88 | 88 | 88 | 88 | 88 | 88 | 88 | 88 |
| | Thickness | mm | 0.38 | 0.38 | 0.38 | 0.38 | 0.38 | 0.38 | 0.38 | 0.78 |

TABLE 1-continued

|  |  |  | Example 1 | Example 2 | Example 3 | Example 4 | Example 5 | Example 6 | Comparative Example 1 | Comparative Example 2 |
|---|---|---|---|---|---|---|---|---|---|---|
| Light control body | Visible light transmittance | % | 70 | 70 | 70 | 70 | 70 | 70 | 70 | 70 |
|  | Thickness | mm | 1.5 | 3 | 3 | 1.5 | 1.5 | 3 | 1.5 | 1.5 |
| Ratio of thickness (Light control body/Ultraviolet absorbing layer) |  |  | 3.9 | 7.9 | 7.9 | 3.9 | 3.9 | 7.9 | 3.9 | 1.9 |
| Glass structure | Visible light transmittance | % | 70 | 70 | 70 | 70 | 70 | 70 | 70 | 70 |
|  | Light resistance test | ΔE | 1.5 | 1.5 | 2 | 1.5 | 1.5 | 1.2 | 6.3 | 6.3 |
|  | Color change after light resistance test | Presence or absence | Absent | Absent | Absent | Absent | Absent | Absent | Present | Present |
|  | Penetration resistance |  | A | A | A | A | A | A | A | A |

\* The visible light transmittances of a light control body and glass structure were measured when a voltage was applied to the light control body in Examples 1, 2, 4, and 5 and Comparative Example 1, and when a voltage was not applied in Examples 3 and 6.
\*\* % in Tables 1 to 4 means % by mass. Formulation in Tables 1 to 4 is formulation of an ultraviolet absorbing layer.

In Examples 1 to 6, the ultraviolet absorbing layer had a maximum transmittance of 10% or less in a wavelength region of 370 nm or more and 400 nm or less and a maximum transmittance of 50% or more in a wavelength region of more than 400 nm and 420 nm or less, and the ratio of a transmittance of 405 nm to a transmittance at 395 nm was 12 or more. Therefore, the glass structure which substantially had no color change even after a light resistance test and was likely to be deteriorated by sunlight could be obtained. Furthermore, when a voltage was applied to the light control body in Examples 1, 2, 4, and 5, and when a voltage was not applied to the light control body in Examples 3 and 6, the glass structure was colorless and transparent.

Meanwhile, in Comparative Examples 1 and 2, the maximum transmittance in a wavelength region of 370 nm or more and 400 nm or less was more than 10%, and the ratio of a transmittance at 405 nm to a transmittance at 395 nm was less than 12, whereby color change that was induced by a light resistance test was observed therein, and thus, a glass structure which is less likely to be deteriorated by sunlight could not be obtained.

Examples 7 to 19, Comparative Examples 3 to 7

A glass structure was produced in the same manner as in Example 1, except that the kinds and contents of a resin, plasticizer, antioxidant, first ultraviolet absorber, and second ultraviolet absorber comprised in an ultraviolet absorbing layer were set to values described in Table 2.

However, in the case when the ultraviolet absorbing layer did not contain the first ultraviolet absorber, the second adhesion layer was produced as with the ultraviolet absorbing layer. In the case when the ultraviolet absorbing layer contained the first ultraviolet absorber, components were mixed in the same proportions, except that the first ultraviolet absorber was not contained, to produce the second adhesion layer as with the ultraviolet absorbing layer.

TABLE 2

|  |  |  | Example 7 | Example 8 | Example 10 | Example 11 | Example 13 | Example 14 | Example 15 |
|---|---|---|---|---|---|---|---|---|---|
| Thermoplastic resin | Kind | — | PVB | PVB | PVB | PVB | PVB | PVB | PVB |
|  | Content | % | 71.4 | 71.4 | 71.4 | 71.4 | 71.4 | 71.4 | 71.4 |
| Plasticizer | Kind | — | 3GO | 3GO | 3GO | 3GO | 3GO | 3GO | 3GO |
|  | Content | % | 27.4 | 27.7 | 27.6 | 2.74 | 27.7 | 27.6 | 27.7 |
| Antioxidant | Kind | — | BHT | BHT | BHT | BHT | BHT | BHT | BHT |
|  | Content | % | 0.14 | 0.14 | 0.14 | 0.14 | 0.14 | 0.14 | 0.14 |
| First ultraviolet absorber | Kind | — | Tinuvin Carbo Protect | Tinuvin Carbo Protect | Tinuvin Carbo Protect | Tinuvin Carbo Protect | Tinuvin Carbo Protect | Tinuvin Carbo Protect | Tinuvin Carbo Protect |
|  | Content | % | 0.043 | 0.022 | 0.021 | 0.043 | 0.043 | 0.043 | 0.052 |
| Second ultraviolet absorber | Kind | — | Tinuvin 326 | Tinuvin 326 | Tinuvin 326 | Tinuvin 326 | Tinuvin 326 | Tinuvin 326 | Eversorb 109 |
|  | Content | % | 0.73 | 0.37 | 0.52 | 0.73 | 0.36 | 0.52 | 0.43 |
| Other additive | Kind | — | — | — | — | — | — | — | — |
|  | Content | % | — | — | — | — | — | — | — |
| Light control body | Kind | — | Liquid crystal PVB | Liquid crystal PVB | Liquid crystal PVB | Liquid crystal PVB | Liquid crystal PVB | Liquid crystal PVB | Liquid crystal PVB |
| Power supply OFF |  |  | Opaque | Opaque | Opaque | Opaque | Opaque | Opaque | Opaque |
| Power supply ON |  |  | Transparent | Transparent | Transparent | Transparent | Transparent | Transparent | Transparent |
| Ultraviolet absorbing layer | Maximum transmittance in 370 or more and 400 nm or less | % | 0.6 | 4.8 | 3.0 | 4.0 | 1.8 | 74 | 4.8 |
|  | Maximum transmittance in more than 400 nm and 420 nm or less | % | 52.7 | 68.4 | 57.9 | 63.0 | 57.0 | 69.3 | 55.6 |

TABLE 2-continued

|  |  |  |  |  |  |  |  |  |
|---|---|---|---|---|---|---|---|---|
|  | Ratio of transmittance 405 nm/395 nm | % | 83.6 | 17.5 | 26.6 | 21.8 | 52.4 | 15.4 | 12.6 |
|  | Visible light transmittance | % | 88 | 88 | 88 | 88 | 88 | 88 | 88 |
|  | Thickness | mm | 0.76 | 0.76 | 0.76 | 0.5 | 0.76 | 0.38 | 0.76 |
| Light control body | Visible light transmittance | % | 70 | 70 | 70 | 70 | 70 | 70 | 70 |
|  | Thickness | mm | 1.5 | 1.5 | 1.5 | 1.5 | 1.5 | 1.5 | 1.5 |
| Ratio of thickness (Light control body/Ultraviolet absorbing layer) |  |  | 2.0 | 2.0 | 2.0 | 3.0 | 2.0 | 3.9 | 2.0 |
| Glass structure | Visible light transmittance | % | 70 | 70 | 70 | 70 | 70 | 70 | 70 |
|  | Light resistance test | ΔE | 1 | 1.6 | 1.1 | 1.2 | 1.4 | 1.7 | 1.3 |
|  | Color change after light resistance test | Presence or absence | Absent | Absent | Absent | Absent | Absent | Absent | Absent |
|  | Penetration resistance |  | A | A | A | A | A | A | A |

|  |  |  | Example 16 | Example 17 | Example 18 | Example 19 | Comparative Example 3 |
|---|---|---|---|---|---|---|---|
| Thermoplastic resin | Kind | — | PVB | PVB | PVB | PVB | PVB |
|  | Content | % | 71.4 | 71.4 | 71.4 | 71.4 | 71.4 |
| Plasticizer | Kind | — | 3GO | 3GO | 3GO | 3GO | 3GO |
|  | Content | % | 27.7 | 27.2 | 27.2 | 27.2 | 27.7 |
| Antioxidant | Kind | — | BHT | BHT | BHT | BHT | BHT |
|  | Content | % | 0.14 | 0.14 | 0.14 | 0.14 | 0.14 |
| First ultraviolet absorber | Kind | — | Tinuvin Carbo Protect | Tinuvin Carbo Protect | Tinuvin Carbo Protect | Tinuvin Carbo Protect | Indole |
|  | Content | % | 0.043 | 0.1 | 0.052 | 0.026 | 0.005 |
| Second ultraviolet absorber | Kind | — | Eversorb 88 | Eversorb 109 | Eversorb 109 | Eversorb 109 | DAINSORB T53 |
|  | Content | % | 0.43 | 0.86 | 0.86 | 0.86 | 0.4 |
| Other additive | Kind | — | — | — | — | — | — |
|  | Content | % | — | — | — | — | — |
| Light control body | Kind | — | Liquid crystal PVB | Liquid crystal PVB | Liquid crystal PVB | Liquid crystal PVB | Liquid crystal PVB |
| Power supply OFF |  |  | Opaque | Opaque | Opaque | Opaque | Opaque |
| Power supply ON |  |  | Transparent | Transparent | Transparent | Transparent | Transparent |
| Ultraviolet absorbing layer | Maximum transmittance in 370 or more and 400 nm or less | % | 5.1 | 3.6 | 1.4 | 3.9 | 15.0 |
|  | Maximum transmittance in more than 400 nm and 420 nm or less | % | 60.4 | 51.9 | 53.5 | 68.1 | 58.1 |
|  | Ratio of transmittance 405 nm/395 nm | % | 16.2 | 14.0 | 80.6 | 54.9 | 3.9 |
|  | Visible light transmittance | % | 88 | 88 | 88 | 88 | 88 |
|  | Thickness | mm | 0.76 | 0.38 | 0.76 | 0.76 | 0.76 |
| Light control body | Visible light transmittance | % | 70 | 70 | 70 | 70 | 70 |
|  | Thickness | mm | 1.5 | 1.5 | 1.5 | 1.5 | 1.5 |
| Ratio of thickness (Light control body/Ultraviolet absorbing layer) |  |  | 2.0 | 3.9 | 2.0 | 2.0 | 2.0 |
| Glass structure | Visible light transmittance | % | 70 | 70 | 70 | 70 | 70 |
|  | Light resistance test | ΔE | 1.6 | 1.2 | 1.1 | 1.8 | 12.5 |
|  | Color change after light resistance test | Presence or absence | Absent | Absent | Absent | Absent | Present |
|  | Penetration resistance |  | A | A | A | A | A |

TABLE 2-continued

| | | | Comparative Example 4 | Comparative Example 5 | Comparative Example 6 | Comparative Example 7 |
|---|---|---|---|---|---|---|
| Thermoplastic resin | Kind | — | PVB | PVB | PVB | PVB |
| | Content | % | 71.4 | 71.4 | 71.4 | 71.4 |
| Plasticizer | Kind | — | 3GO | 3GO | 3GO | 3GO |
| | Content | % | 28 | 27.9 | 27.9 | 28 |
| Antioxidant | Kind | — | BHT | BHT | BHT | BHT |
| | Content | % | 0.14 | 0.14 | 0.14 | 0.1 |
| First ultraviolet absorber | Kind | — | Indole | — | Indole | — |
| | Content | % | 0.01 | — | 0.009 | — |
| Second ultraviolet absorber | Kind | — | DAINSORB T53 | Tinuvin 1600 | Tinuvin 1600 | Tinuvin 326 |
| | Content | % | 0.14 | 0.28 | 0.21 | 0.14 |
| Other additive | Kind | — | — | — | — | — |
| | Content | % | — | — | — | — |
| Light control body | Kind | — | Liquid crystal PVB | Liquid crystal PVB | Liquid crystal PVB | Liquid crystal PVB |
| Power supply OFF | | | Opaque | Opaque | Opaque | Opaque |
| Power supply ON | | | Transparent | Transparent | Transparent | Transparent |
| Ultraviolet absorbing layer | Maximum transmittance in 370 or more and 400 nm or less | % | 8.7 | 40.0 | 9.5 | 29.1 |
| | Maximum transmittance in more than 400 nm and 420 nm or less | % | 51.0 | 80.2 | 52.0 | 69.4 |
| | Ratio of transmittance 405 nm/395 nm | % | 2.7 | 2.7 | 2.6 | 4.7 |
| | Visible light transmittance | % | 88 | 88 | 88 | 88 |
| | Thickness | mm | 0.76 | 0.76 | 0.76 | 0.76 |
| Light control body | Visible light transmittance | % | 70 | 70 | 70 | 70 |
| | Thickness | mm | 1.5 | 1.5 | 1.5 | 1.5 |
| Ratio of thickness (Light control body/Ultraviolet absorbing layer) | | | 2.0 | 2.0 | 2.0 | 2.0 |
| Glass structure | Visible light transmittance | % | 70 | 70 | 7.5 | 70 |
| | Light resistance test | ΔE | 8.5 | 15 | 12 | 6.6 |
| | Color change after light resistance test | Presence or absence | Present | Present | Present | Present |
| | Penetration resistance | | A | A | A | A |

* The visible light transmittances of a light control body and glass structure were measured when a voltage was applied to the light control body in Examples 7 to 19 and Comparative Examples 3 to 7.

In Examples 7 to 19, the ultraviolet absorbing layer had a maximum transmittance of 10% or less in a wavelength region of 370 nm or more and 400 nm or less and a maximum transmittance of 50% or more in a wavelength region of more than 400 nm and 420 nm or less, and the ratio of a transmittance of 405 nm to a transmittance at 395 nm was 12 or more. Therefore, the glass structure which substantially had no color change even after a light resistance test and was less likely to be deteriorated by sunlight could be obtained. When a voltage was applied to the light control body in Examples 7 to 19, the glass structure was colorless and transparent.

Meanwhile, in Comparative Examples 3 to 7, the maximum transmittance in a wavelength region of 370 nm or more and 400 nm or less was more than 10%, or the ratio of a transmittance of 405 nm to a transmittance at 395 nm was less than 12, whereby color change that was induced by a light resistance test was observed therein, and thus, a glass structure which is less likely to be deteriorated by sunlight could not be obtained.

Example 20

(1) Production of Ultraviolet Absorbing Layer

A PVB, a plasticizer, an ITO as an infrared absorbing agent, an antioxidant, a benzotriazole-based compound (1) as a first ultraviolet absorber, and a benzotriazole-based compound (2) as a second ultraviolet absorber were mixed such that the contents of the PVB, plasticizer, ITO, antioxidant, benzotriazole-based compound (1), and benzotriazole-based compound (2) in an ultraviolet absorbing layer were respectively set to 71.21% by mass, 27.3% by mass, 0.15% by mass, 0.29% by mass, 0.022% by mass, and 0.58% by mass. The mixture was subjected to extrusion molding with a biaxial anisotropic extruder to produce an ultraviolet absorbing layer having a film thickness of 380 μm. When the compounds were mixed, an organic acid magnesium aqueous solution as an adhesion control agent was further added into the mixture such that a Mg concentration in the ultraviolet absorbing layer was set to 65 ppm.

(2) Production of Second Adhesion Layer

Components were mixed in the same proportions, except that 0.022% by mass of a benzotriazole-based compound (1) was not contained, to produce a second adhesion layer as with the ultraviolet absorbing layer.

A light control body and a glass structure were produced in the same manner as in Example 1 in the subsequent procedure.

Examples 21 and 22

Examples 21 and 22 were carried out in the same manner as in Example 20, except that the kinds and contents of a resin, plasticizer, antioxidant, first ultraviolet absorber, and second ultraviolet absorber in an ultraviolet absorbing layer were changed to values described in Table 3, and an STN liquid crystal cell was used as a light control body. When a voltage was not applied between transparent electrodes, a light control body and a glass structure were opaque. When a voltage of 12 V was applied, the light control body and the glass structure were transparent.

Examples 23 to 30, Comparative Examples 8 to 14

A glass structure was produced in the same manner as in Example 20, except that the kinds and contents of a resin, plasticizer, antioxidant, first ultraviolet absorber, and second ultraviolet absorber in an ultraviolet absorbing layer were set to values described in Tables 3 and 4.

However, in Examples 21 to 30 and Comparative Examples 8 to 14, in the case when the ultraviolet absorbing layer did not contain the first ultraviolet absorber, the second adhesion layer was produced as with the ultraviolet absorbing layer. In the case when the ultraviolet absorbing layer contained the first ultraviolet absorber, components were mixed in the same proportions, except that the first ultraviolet absorber was not contained, to produce the second adhesion layer as with the ultraviolet absorbing layer.

TABLE 3

| | | | Example 20 | Example 21 | Example 22 | Example 23 | Example 24 | Example 25 |
|---|---|---|---|---|---|---|---|---|
| Thermoplastic resin | Kind | — | PVB | PVB | PVB | PVB | PVB | PVB |
| | Content | % | 71.21 | 71.21 | 71.2 | 71.18 | 71.4 | 71.4 |
| Plasticizer | Kind | — | 3GO | 3GO | 3GO | 3GO | 3GO | 3GO |
| | Content | % | 27.3 | 27.2 | 27.3 | 27.3 | 27.6 | 27.7 |
| Heat shielding agent | Kind | — | ITO | ITO | ITO | ITO | ITO | ITO |
| | Content | % | 0.15 | 0.15 | 0.15 | 0.15 | 0.15 | 0.15 |
| Antioxidant | Kind | — | BHT | BHT | BHT | BHT | BHT | BHT |
| | Content | % | 0.29 | 0.29 | 0.29 | 0.29 | 0.29 | 0.29 |
| First ultraviolet absorber | Kind | — | Tinuvin Carbo Protect | Tinuvin Carbo Protect | Tinuvin Carbo Protect | Tinuvin Carbo Protect | Tinuvin Carbo Protect | Tinuvin Carbo Protect |
| | Content | % | 0.022 | 0.043 | 0.043 | 0.043 | 0.044 | 0.014 |
| Second ultraviolet absorber | Kind | — | Tinuvin 326 | Tinuvin 326 | Tinuvin 326 | Tinuvin 326 | Tinuvin 326 | Tinuvin 326 |
| | Content | % | 0.58 | 0.73 | 0.52 | 0.58 | 0.29 | 0.29 |
| Light control body | Kind | — | Liquid crystal PVB | STN liquid crystal | STN liquid crystal | Liquid crystal PVB | Liquid crystal PVB | Liquid crystal PVB |
| Power supply OFF | | | Opaque | Opaque | Opaque | Opaque | Opaque | Opaque |
| Power supply ON | | | Transparent | Transparent | Transparent | Transparent | Transparent | Transparent |
| Ultraviolet absorbing layer | Maximum transmittance in 370 or more and 400 nm or less | % | 9.6 | 4.1 | 8.2 | 6.7 | 3.6 | 9.7 |
| | Maximum transmittance in more than 400 nm and 420 nm or less | % | 73.5 | 66.3 | 67.8 | 67.4 | 55.5 | 70.7 |
| | Ratio of transmittance 405 nm/395 nm | % | 14.6 | 33.1 | 12.8 | 16.7 | 18.4 | 12.5 |
| | Visible light transmittance | % | 88 | 88 | 88 | 88 | 88 | 88 |
| | Thickness | mm | 0.38 | 0.38 | 0.38 | 0.38 | 0.76 | 0.76 |
| Light control body | Visible light transmittance | % | 70 | 70 | 70 | 70 | 70 | 70 |
| | Thickness | mm | 1.5 | 3 | 1.5 | 1.5 | 1.5 | 1.5 |
| Ratio of thickness (Light control body/Ultraviolet absorbing layer) | | | 3.9 | 7.9 | 3.9 | 3.9 | 2.0 | 2.0 |
| Glass structure | Visible light transmittance | % | 69 | 69 | 69 | 69 | 69 | 69 |
| | Light resistance test | ΔE | 1.2 | 1.2 | 1.2 | 1.2 | 0.8 | 1.3 |
| | Color change after light resistance test | Presence or absence | Absent | Absent | Absent | Absent | Absent | Absent |
| | Penetration resistance | | A | A | A | A | A | A |

TABLE 3-continued

|  |  |  | Example 26 | Example 27 | Example 28 | Example 29 | Example 30 |
|---|---|---|---|---|---|---|---|
| Thermoplastic resin | Kind | — | PVB | PVB | PVB | PVB | PVB |
|  | Content | % | 71.4 | 71.4 | 71.4 | 71.4 | 71.4 |
| Plasticizer | Kind | — | 3GO | 3GO | 3GO | 3GO | 3GO |
|  | Content | % | 27.4 | 27.2 | 27.7 | 27.4 | 26.9 |
| Heat shielding agent | Kind | — | ITO | ITO | ITO | ITO | ITO |
|  | Content | % | 0.15 | 0.15 | 0.15 | 0.15 | 0.15 |
| Antioxidant | Kind | — | BHT | BHT | BHT | BHT | BHT |
|  | Content | % | 0.29 | 0.29 | 0.29 | 0.29 | 0.29 |
| First ultraviolet absorber | Kind | — | Tinuvin Carbo Protect | Indole | Coumarin | Tinuvin Carbo Protect | Tinuvin Carbo Protect |
|  | Content | % | 0.014 | 0.01 | 0.014 | 0.04 | 0.09 |
| Second ultraviolet absorber | Kind | — | Tinuvin 326 | Tinuvin 326 | Tinuvin 326 | Eversorb 88 | Eversorb 109 |
|  | Content | % | 0.58 | 0.73 | 0.73 | 0.43 | 0.86 |
| Light control body | Kind | — | Liquid crystal PVB | Liquid crystal PVB | Liquid crystal PVB | Liquid crystal PVB | Liquid crystal PVB |
| Power supply OFF |  |  | Opaque | Opaque | Opaque | Opaque | Opaque |
| Power supply ON |  |  | Transparent | Transparent | Transparent | Transparent | Transparent |
| Ultraviolet absorbing layer | Maximum transmittance in 370 or more and 400 nm or less | % | 1.4 | 4.7 | 4.8 | 4.5 | 3.0 |
|  | Maximum transmittance in more than 400 nm and 420 nm or less | % | 66.2 | 67.5 | 68.8 | 55.4 | 50.8 |
|  | Ratio of transmittance 405 nm/395 nm | % | 120.0 | 17.5 | 18.0 | 15.2 | 14.0 |
|  | Visible light transmittance | % | 88 | 88 | 88 | 88 | 88 |
|  | Thickness | mm | 0.76 | 0.38 | 0.38 | 0.76 | 0.38 |
| Light control body | Visible light transmittance | % | 70 | 70 | 70 | 70 | 70 |
|  | Thickness | mm | 1.5 | 1.5 | 1.5 | 1.5 | 1.5 |
| Ratio of thickness (Light control body/Ultraviolet absorbing layer) |  |  | 2.0 | 3.9 | 3.9 | 2.0 | 3.9 |
| Glass structure | Visible light transmittance | % | 69 | 69 | 69 | 69 | 69 |
|  | Light resistance test | ΔE | 0.9 | 1 | 1.1 | 1.3 | 0.9 |
|  | Color change after light resistance test | Presence or absence | Absent | Absent | Absent | Absent | Absent |
|  | Penetration resistance |  | A | A | A | A | A |

* The visible light transmittances of a light control body and glass structure were measured when a voltage was applied to the light control body in Examples 20 to 30.

TABLE 4

|  |  |  | Comparative Example 8 | Comparative Example 9 | Comparative Example 10 | Comparative Example 11 | Comparative Example 12 | Comparative Example 13 | Comparative Example 14 |
|---|---|---|---|---|---|---|---|---|---|
| Thermoplastic resin | Kind | — | PVB | PVB | PVB | PVB | PVB | PVB | PVB |
|  | Content | % | 71.4 | 71.4 | 71.4 | 71.4 | 71.4 | 71.4 | 71.4 |
| Plasticizer | Kind | — | 3GO | 3GO | 3GO | 3GO | 3GO | 3GO | 3GO |
|  | Content | % | 27.4 | 27.4 | 27.4 | 27.7 | 27.5 | 27.6 | 27.9 |
| Heat shielding agent | Kind | — | ITO | ITO | ITO | ITO | ITO | ITO | ITO |
|  | Content | % | 0.15 | 0.15 | 0.15 | 0.15 | 0.15 | 0.15 | 0.15 |
| Antioxidant | Kind | — | BHT | BHT | BHT | BHT | BHT | BHT | BHT |
|  | Content | % | 0.29 | 0.29 | 0.29 | 0.29 | 0.29 | 0.29 | 0.1 |
| First ultraviolet absorber | Kind | — | — | — | Indole | Indole | — | Indole | — |
|  | Content | % | — | — | 0.005 | 0.01 | — | 0.009 | — |
| Second ultraviolet absorber | Kind | — | Tinuvin 326 | Tinuvin 326 | DAINSORB T53 | DAINSORB T53 | Tinuvin 1600 | Tinuvin 1600 | Tinuvin 326 |
|  | Content | % | 0.29 | 0.41 | 0.4 | 0.14 | 0.28 | 0.21 | 0.14 |

TABLE 4-continued

|  |  |  | Comparative Example 8 | Comparative Example 9 | Comparative Example 10 | Comparative Example 11 | Comparative Example 12 | Comparative Example 13 | Comparative Example 14 |
|---|---|---|---|---|---|---|---|---|---|
| Light control body | Kind | — | Liquid crystal | Liquid crystal | Liquid crystal | Liquid crystal | Liquid crystal | Liquid crystal | Liquid crystal |
|  | Power supply OFF |  | PVB Opaque | PVB Opaque | PVB Opaque | PVB Opaque | PVB Opaque | PVB Opaque | PVB Opaque |
|  | Power supply ON |  | Transparent | Transparent | Transparent | Transparent | Transparent | Transparent | Transparent |
| Ultraviolet absorbing layer | Maximum transmittance in 370 or more and 400 nm or less | % | 14.9 | 24.8 | 14.5 | 8.5 | 39.5 | 9.0 | 28.6 |
|  | Maximum transmittance in more than 400 nm and 420 nm or less | % | 78.4 | 80.5 | 57.1 | 50.0 | 79.5 | 51.0 | 68.3 |
|  | Ratio of transmittance 405 nm/395 nm | % | 10.6 | 5.3 | 4.0 | 2.8 | 2.8 | 2.7 | 4.8 |
|  | Visible light transmittance | % | 88 | 88 | 88 | 88 | 88 | 88 | 88 |
|  | Thickness | mm | 0.76 | 0.38 | 0.76 | 0.76 | 0.76 | 0.76 | 0.76 |
| Light control body | Visible light transmittance | % | 70 | 70 | 70 | 70 | 70 | 70 | 70 |
|  | Thickness | mm | 1.5 | 1.5 | 1.5 | 1.5 | 1.5 | 1.5 | 1.5 |
| Ratio of thickness (Light control body/Ultraviolet absorbing layer) |  |  | 2.0 | 3.9 | 2.0 | 2.0 | 2.0 | 2.0 | 2.0 |
| Glass structure | Visible light transmittance | % | 69 | 69 | 69 | 69 | 69 | 69 | 69 |
|  | Light resistance test | ΔE | 5.1 | 5.1 | 10 | 6.8 | 1.2 | 0.9 | 5.3 |
|  | Color change after light resistance test | Presence or absence | Present | Present | Present | Present | Present | Present | Present |
|  | Penetration resistance |  | A | A | A | A | A | A | A |

\* The visible light transmittances of a light control body and glass structure were measured when a voltage was applied to the light control body in Comparative Examples 8 to 14.

In Examples 20 to 30, the ultraviolet absorbing layer had a maximum transmittance of 10% or less in a wavelength region of 370 nm or more and 400 nm or less and a maximum transmittance of 50% or more in a wavelength region of more than 400 nm and 420 nm or less, and the ratio of a transmittance at 405 nm to a transmittance at 395 nm was 12 or more. Therefore, the glass structure which substantially had no color change even after a light resistance test and was less likely to be deteriorated by sunlight could be obtained. Furthermore, when a voltage was applied to the light control body in Examples 20 to 30, the glass structure was colorless and transparent.

Meanwhile, in Comparative Examples 8 to 14, the maximum transmittance in a wavelength region of 370 nm or more and 400 nm or less was more than 10%, or the ratio of a transmittance at 405 nm to a transmittance at 395 nm was less than 12, whereby color change that was induced by a light resistance test was observed therein, and thus, a glass structure which is less likely to be deteriorated by sunlight could not be obtained.

REFERENCE SIGNS LIST

10 glass structure
11 first glass plate
12 second glass plate
13 light control body
14 ultraviolet absorbing layer (first adhesion layer)
15 second adhesion layer

The invention claimed is:

1. A glass structure comprising:
a pair of glass plates;
a light control body disposed between the pair of glass plates; and
an ultraviolet absorbing layer disposed between the light control body and one of the glass plates,
the ultraviolet absorbing layer having a maximum transmittance of 10% or less in a wavelength region of 370 nm or more and 400 nm or less and a maximum transmittance of 50% or more in a wavelength region of more than 400 nm and 420 nm or less,
a ratio of a transmittance at 405 nm to a transmittance at 395 nm being 12 or more.

2. The glass structure according to claim 1, wherein a ratio of a thickness of the light control body to that of the ultraviolet absorbing layer is 0.5 to 10.5.

3. The glass structure according to claim 1, wherein the ultraviolet absorbing layer comprises at least one thermoplastic resin selected from the group consisting of a polyvinyl acetal resin, an ethylene-vinyl acetate copolymer resin, and an ionomer resin.

4. The glass structure according to claim 1, wherein the ultraviolet absorbing layer comprises a polyvinyl acetal resin and a plasticizer.

5. The glass structure according to claim 1, wherein the light control body comprises any one of a liquid crystal layer and an electrochromic layer.

6. The glass structure according to claim 1, wherein the ultraviolet absorbing layer comprises an ultraviolet absorber.

7. The glass structure according to claim 6, wherein the ultraviolet absorber comprises at least one selected from the group consisting of an indole-based compound, a benzotriazole-based compound, and a coumarin-based compound.

8. The glass structure according to claim 7, wherein the indole-based compound is a compound represented by the following formula (1),

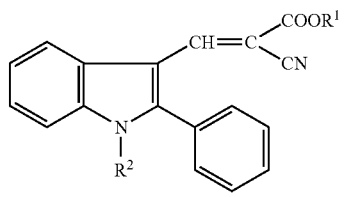

wherein:
$R^1$ represents an alkyl group having 1 to 3 carbon atoms; and
$R^2$ represents a hydrogen atom, an alkyl group having 1 to 10 carbon atoms, or an aralkyl group having 7 to 10 carbon atoms.

9. The glass structure according to claim 7, wherein the benzotriazole-based compound is a compound represented by the following formula (2),

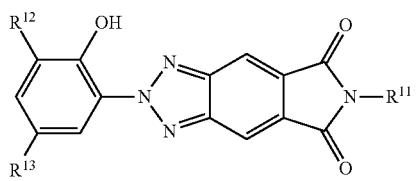

wherein:
$R^{11}$ represents an alkyl group having 1 to 10 carbon atoms; and
$R^{12}$ and $R^{13}$ each independently represent a hydrogen atom, an alkyl group having 1 to 10 carbon atoms, or an aralkyl group having 7 to 12 carbon atoms.

10. The glass structure according to claim 7, further comprising a compound having a highest absorption maximum in a wavelength region of 330 to 380 nm.

11. The glass structure according to claim 10, wherein the compound having a highest absorption maximum in a wavelength region of 330 to 380 nm is a compound represented by the following formula (3),

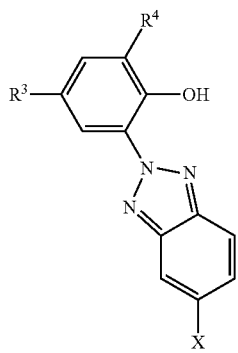

wherein:
$R^3$ represents a hydrogen atom, an alkyl group having 1 to 8 carbon atoms, or an alkoxycarbonylalkyl group having 4 to 20 carbon atoms;
$R^4$ represents a hydrogen atom or an alkyl group having 1 to 8 carbon atoms; and
X is a chlorine atom or a hydrogen atom.

12. The glass structure according to claim 1, further comprising an adhesion layer disposed between the light control body and the other glass.

13. The glass structure according to claim 12, wherein the adhesion layer comprises at least one thermoplastic resin selected from the group consisting of a polyvinyl acetal resin, an ethylene-vinyl acetate copolymer resin, and an ionomer resin.

14. The glass structure according to claim 12, wherein the adhesion layer comprises a polyvinyl acetal and a plasticizer.

15. The glass structure according to claim 12, wherein a ratio of a thickness of the light control body to that of the adhesion layer is 0.5 to 10.5.

16. The glass structure according to claim 1 used for an outdoor window.

* * * * *